US012760267B2

(12) United States Patent
Hoehnel et al.

(10) Patent No.: US 12,760,267 B2
(45) Date of Patent: Oct. 13, 2026

(54) ORGANOID ARRAYS

(71) Applicant: Ecole Polytechnique Fèdèrale de Lausanne, Lausanne (CH)

(72) Inventors: Sylke Hoehnel, Lausanne (CH); Nathalie Brandenberg, Lausanne (CH); Matthias Lutolf, St. Sulpice (CH)

(73) Assignee: Ecole Polytechnique Fèdèrale de Lausanne, Lausanne (CH)

( * ) Notice: Subject to any disclaimer, the term of this patent is extended or adjusted under 35 U.S.C. 154(b) by 694 days.

(21) Appl. No.: 16/334,061

(22) PCT Filed: Sep. 15, 2017

(86) PCT No.: PCT/EP2017/073357

§ 371 (c)(1),
(2) Date: Mar. 18, 2019

(87) PCT Pub. No.: WO2018/050862

PCT Pub. Date: Mar. 22, 2018

(65) Prior Publication Data

US 2020/0010797 A1 Jan. 9, 2020

(30) Foreign Application Priority Data

Sep. 19, 2016 (EP) .................................... 16189510

(51) Int. Cl.
*C12N 5/00* (2006.01)
*B01L 3/00* (2006.01)
(Continued)

(52) U.S. Cl.
CPC ........ *C12N 5/0062* (2013.01); *B01L 3/50857* (2013.01); *C12M 23/12* (2013.01);
(Continued)

(58) Field of Classification Search
CPC .... C12N 5/0062; C12N 5/062; C12N 5/0631; C12N 5/068; C12N 2506/02;
(Continued)

(56) References Cited

U.S. PATENT DOCUMENTS

2009/0220565 A1* 9/2009 Guldner .................... A61P 9/00
435/373
2011/0171712 A1 7/2011 Rivron et al.
(Continued)

FOREIGN PATENT DOCUMENTS

WO WO-2014180970 A1 * 11/2014 ............... C12N 5/00
WO 2016103002 A1 6/2016
(Continued)

OTHER PUBLICATIONS

Decembrini et al. "Micro-culture arrays to control the generation of retinal organoids" ARVO 2016 Annual Meeting Abstracts (Year: 2016). Document provided on IDS document dated Mar. 18, 2019.*
(Continued)

*Primary Examiner* — Tracy Vivlemore
*Assistant Examiner* — Lauren K Van Buren
(74) *Attorney, Agent, or Firm* — Muncy, Geissler, Olds & Lowe, P.C.

(57) ABSTRACT

The invention provides methods for producing arrays of organoids, the arrays thereof and uses of such arrays.

9 Claims, 9 Drawing Sheets

(51) Int. Cl.
*C12M 1/32* (2006.01)
*C12N 5/071* (2010.01)
*C12N 5/0793* (2010.01)
*G01N 33/50* (2006.01)

(52) U.S. Cl.
CPC ........... *C12N 5/062* (2013.01); *C12N 5/0631* (2013.01); *C12N 5/068* (2013.01); *G01N 33/5073* (2013.01); *C12N 2506/02* (2013.01); *C12N 2531/00* (2013.01); *G01N 2500/10* (2013.01)

(58) Field of Classification Search
CPC ............. C12N 2531/00; B01L 3/50857; B01L 3/5085; C12M 23/12; G01N 33/5073; G01N 2500/10; G01N 33/5082
See application file for complete search history.

(56) References Cited

U.S. PATENT DOCUMENTS

2014/0227784 A1* 8/2014 Ejiri .................... C12N 5/0693 435/395
2017/0283766 A1* 10/2017 Hribar .................. B29C 64/129

FOREIGN PATENT DOCUMENTS

WO 2016112344 A1 7/2016
WO 2016141137 A1 9/2016

OTHER PUBLICATIONS

Loessner et al. "Hydrogel Microwell Arrays Allow the Assessment of Protease-Associated Enhancement of Cancer Cell Aggregation and Survival." Microarrays 2013, 2, 208-227. (Year: 2013).*
Decembrini et al., "ARVO 2016 Annual Meeting Abstracts Micro-Culture Arrays to Control the Generation of Retinal Organoids", May 1, 2016.
Vrij et al., "3D High Throughput Screening and Profiling of Embryoid Bodies in Thermoformed Microwell Plates", Lab on a Chip, vol. 16, No. 4, Jan. 1, 2016.
Allbritton et al., "Colonic Organoid Array on a Biomimetic, Microengineered Hydrogel Scaffold." 19th International Conference on Miniaturized Systems for Chemistry and Life Sciences, MicroTAS 2015. Chemical and Biological Microsystems Society, 2015.
N.N, "AggreWell", Dec. 1, 2016.
International Search Report and Written Opinion dated Nov. 10, 2017 for corresponding International Patent Application No. PCT/EP2017/073357.
Abberton, K.M., et al. (2008). "Myogel, a novel, basement membrane-rich, extracellular matrix derived from skeletal muscle, is highly adipogenic in vivo and in vitro." Cells Tissues Organs 188, 347-358.
Brandenberg, N., et al. (2016). "In Situ Patterning of Microfluidic Networks in 3D Cell-Laden Hydrogels" Adv. Mater. 28, 7450-7456.
Debnath, J., (2003). "Morphogenesis and oncogenesis of MCF-10A mammary epithelial acini grown in three-dimensional basement membrane cultures." Methods San Diego Calif 30, 256-268.
Decembrini, S., et al. (2014). "Derivation of Traceable and Transplantable Photoreceptors from Mouse Embryonic Stem Cells." Stem Cell Rep. 2, 853-865.
Ehrbar, M., et al. (2007a). "Enzymatic formation of modular cell-instructive fibrin analogs for tissue engineering." Biomaterials 28, 3856-3866.
Ehrbar, M., et al. (2007b). "Biomolecular Hydrogels Formed and Degraded via Site-Specific Enzymatic Reactions." Biomacromolecules 8, 3000-3007.
Gobaa, S., et al. (2011). "Artificial niche microarrays for probing single stem cell fate in high throughput." Nat. Methods 8, 949-955.
Smith, A.G. "Culture and differentiation of embryonic stem cells." J. Tissue Cult. Methods 13, 89-94.
Dekkers et al. (2013). "A functional CFTR assay using primary cystic fibrosis intestinal organoids." Nat. Med. 19, 939-945.
Ehrbar et al. (2011). "Elucidating the Role of Matrix Stiffness in 3D Cell Migration and Remodeling." Biophys. J. 100, 284-293.
Fatehullah et al. (2016). "Organoids as an in vitro model of human development and disease." Nat. Cell Biol. 18, 246-254.
Gracz et al. (2015). "A high-throughput platform for stem cell niche co-cultures and downstream gene expression analysis." Nat. Cell Biol. 17, 340-349.
Hannan et al. "Generation of multipotent foregut stem cells from human pluripotent stem cells." Stem cell reports 1, 293-306, (2013).
Jourdain et al. "The human CFTR protein expressed in CHO cells activates aquaporin-3 in a cAMP-dependent pathway: study by digital holographic microscopy." (2014) Journal of Cell Science, 127, 546-556.
Jung et al. "Isolation and in vitro expansion of human colonic stem cells." Nature Medicine, Sep. 2011, 17, 1225-1227.
Sato et al. "Single Lgr5 stem cells build crypt-villus structures in vitro without a mesenchymal niche." Nature, vol. 459, 262-265, May 14, 2009.
Shamir et al. "Three-dimensional organotypic culture: experimental models of mammalian biology and disease." Nat. Rev. Mol. Cell Biol. 15, 647-664, Oct. 2014.
Todhunter et al. "Programmed synthesis of three-dimensional tissues." (2015) Nat. Methods 12, 975-981.
Yin et al. "Niche-independent high-purity cultures of Lgr5+ intestinal stem cells and their progeny." (2014) Nat. Methods 11, 106-112.

* cited by examiner

ORGANOID ARRAYS

RELATED APPLICATIONS

The present application is a U.S. National Stage application under 35 USC 371 of PCT Application Serial No. PCT/EP2017/073357, filed on 15 Sep. 2017; which claims priority from EP patent application Ser. No. 16/189,510.7, filed 19 Sep. 2016, the entirety of both of which are incorporated herein by reference.

FIELD OF THE INVENTION

The invention provides methods for producing organoid arrays for high-throughput analysis.

BACKGROUND TO INVENTION

The study of mammalian organs and tissues has been a long lasting challenge as they are difficult to access and analyze in real time (Shamir and Ewald, 2014). As an alternative, whole-organ and organ slices have been conventionally extracted and cultured in vitro. However, the limited diffusion through these explants has restricted this approach to the use of embryonic or thin organs. Recently, major advances in stem cell biology demonstrated that adult and pluripotent stem cells have the capability to survive, grow and differentiate into homeostatic tissue-mimicking structures, or organoids, in vitro, when cultured in three-dimensional matrices. This technological advance is becoming an essential tool for understanding a wide range of biological processes that happen in vivo such as tissue development and homeostasis, stem cell niche functions and tissue responses to drugs, mutations or damage. However, these cultures are still under development and remain variable, which impedes their standard use in pharmaceutical drug screening and therapy development.

Three main limitations to the currently available in vitro organoids can be outlined; (i) the current culture conditions fail to mimic the native microenvironment, i.e. biomechanical forces, growth factors/signaling gradients, which strongly limits the control over organoid growth, (ii) artifacts induced by Matrigel™, a cancer derived matrix that is commonly used as a scaffold for organoid growth, and (iii) a strong heterogeneity in terms of viability, size and shape, distribution and uncontrolled signaling between organoids, impeding phenotypic assay developments (Fatehullah et al., 2016).

The growth of cells in arrays is a standard technique in the field. Cells are seeded into individual wells of a multiwell array plate. Each well of the plate can be subjected to a different assay and/or experimental condition and tracked independently over time. Recently, a number of attempts have been made to grow cell aggregates and organoids in such arrays. However, researchers have found difficulties in forming organoids on conventional array plates formed of plastics, as noted below.

US 2011/0171712, Rivron et al. (Rivron et al., 2011) describes the growth of cell aggregates within the confinement of a micro-array plate. The aggregates are formed by applying a cell suspension on top of a microwell array and allowing the cells to settle in the microarray. Upon spatial confinement in the wells, the cells aggregate spontaneously (column 5, paragraph 4-5). The confined cell aggregates are then harvested from the microwells, induced to undergo cell differentiation and tissue morphogenesis and combined together to form biological tissues (page 4, paragraphs [0038-0042]). The microwells described by Rivron are too small to allow organoid formation within the wells themselves and are therefore limited to the function of growing discrete cell aggregates that must be harvested in order to produce organoids. Rivron does not therefore solve the problem of growing organoids in an array.

Gracz et al. (Gracz et al., 2015) provides microwell plates for culturing and differentiating arrays of intestinal stem cells (ISCs) (Gracz, FIG. 1). The ISCs are randomly seeded into the microwells of the plate such that the array comprises both microwells containing one or more ISCs and empty microwells (page 3, paragraph 4 and FIG. 1F). Image analysis of the arrays therefore relies on computational analysis to identify microwells containing ISCs (FIG. 2A), given that approximately half of the microwells in the plate are empty (FIG. 2I, ~1200 wells out of 2254). The ISC arrays are differentiated into enteroids that grow out from their original microwells as they develop (FIG. 1L). Gracz therefore provides an array of organoids. However, the usefulness of these organoids in high-throughput assays is limited by the need for extensive image processing and analysis in order to exclude empty wells and identify the organoids themselves. Furthermore, the number of experimental conditions or assays permitted per experiment is sub-optimal, given that half of the microwells in an array are empty.

Decembrini et al. (Decembrini et al., 2016) briefly describes the growth of retinal organoids in U-bottom microwell plates. However, Decembrini does not describe what the arrays look like or how they are formed.

Allbriton et al. (Allbriton et al., 2015) provides a microarray scaffold for culturing colonoids (colon organoids). The colonoids are cultured in a collagen matrix, released and then arrayed on the scaffold to generate an array of colonoids within a microwell plate. The microwells are fabricated from collagen and are 150 μm in diameter and 150 μm in height (page 95, paragraph 1). The method of Allbriton results in an array in which the organoids are distributed randomly within their respective microwells (i.e. in the center, or to the side, FIG. 3A). As the colonoids grow within the array they bulge out of the microwells to generate a mushroom shape (FIG. 4) and are therefore no longer within the same 2D plane. Therefore, although Allbriton provides an array of organoids, these organoids must first be grown in a collagen matrix. This limits the use of these arrays for investigating organoid development (as this process does not occur in the array itself). The arrays of Allbriton present a further problem that the organoids are distributed randomly within their respective microwells and are not within the same 2D plane, again presenting a challenge to image analysis of the organoids within the array.

Todhunter et al. (Todhunter et al., 2015) describes arrays of cells embedded in position by DNA-programmed assembly. The cells are first functionalized by incorporation of DNA oligonucleotides into their cell membranes and then attached to glass slides via interaction of these oligonucleotides with complementary sequences within DNA spots fixed to the glass. Multiple rounds of cell adhesion leads to the formation of 3D microtissue structures around the spots. A hydrogel is allowed to form around the fixed cell in order to embed them in position. The gel is then detached from the surface of the glass slides and placed into a culture dish on top of another hydrogel, forming a sandwich culture (Todhunter, FIG. 1). These microarrays are not suitable for producing arrays of stem cells that can develop into organoids, given that the DNA labelling process is likely to affect stem cell function.

Vrij et al (2016) describe an array of embryoid bodies formed in plastic wells. As noted by Vrij et al, the formed embryoid bodies are comparatively small, and that imaging problems may occur with cells located in the periphery of the wells. This imposes certain limitations on the embryoid bodies as described by Vrij et al, and makes such a plastic array-based approach unsuitable for generation of larger organoids.

WO2016/141137 (Harvard) discloses methods to vascularize single organoids through microfluidic interfaces on a chip. It does not teach methods which are able to generate an array of reproducible organoids, tessellated, where organoids can be cultured and traced in the same location over time. Example 3 discusses the use of Aggrewells™ to form embryoid bodies; however after embryoid body formation and to induce organoid formation, the embryoid bodies have to be harvested from the Aggrewells™ and need to be transferred to a different platform which does not allow for planarity or reproducibility.

Therefore, despite numerous attempts to develop organoid arrays suitable for high-throughput analysis, the organoid arrays so far developed are limited by the inefficient use of microwells within the array; the need to develop the organoids in a matrix before being seeded into the array; the need to harvest organoids grown in the array, in order to provide sufficient space for them to develop; and/or the need for invasive techniques for precisely localizing the cells within the array such that the array can be subjected to high-throughput and real-time image analysis.

SUMMARY OF INVENTION

In order to overcome the issues associated with culturing organoids in vitro in a format suitable for high-throughput pharmaceutical drug screening and therapy development, the inventors have developed a new high throughput microwell platform for the reproducible growth of organoids in situ, including their co-culture with other cell types such as stromal cells and their long-term culture. This technology is highly versatile for growing different types of organoids in a controlled fashion.

The inventors demonstrate the automated analysis of these cultures, laying the foundation for the use of these cultures in phenotypic drug screenings and therapy development.

Further, the present invention permits reproducible generation of arrays of organoids, in a manner which was not before considered possible. In particular, aspects of the present invention permit generation of organoids in an array using hydrogel materials that, due to their highly hydrated and soft make-up, have biomimetic physical and chemical properties. Prior art approaches using arrays fabricated from non-hydrated materials such as plastics or glass may not be suitable for organoid generation. A particularly advantageous aspect of the invention permits direct formation of organoids in situ, whereas prior art approaches may necessitate organoid formation outside an array, and subsequent transfer of organoids onto an array, leading to an unequal distribution of organoids of unequal size, as well as a loss of the organoid developmental history. In aspects of the present invention, stem cells are seeded onto a bioengineered or biofunctional hydrogel, and aggregation and organoid formation occur in the specific location where stem cells aggregate and undergo morphogenesis thanks to the architectural and chemical properties of the substrate used. This permits a reproducible process, giving rise to an array of consistently formed organoids arranged in the same plane, thereby providing many advantages for subsequent imaging and analysis, as well as unique traceability and the possibility for clonal analyses.

ABBREVIATIONS 2D two dimensional
3D three-dimensional
96U 96 well U-bottom plates
CFTR cystic fibrosis transmembrane conductance regulator
DHM digital holographic microscopy
ESC embryonic stem cells
ECM extracellular matrix
GFP green fluorescence protein
IPSC induced pluripotent stem cells
MW microwells
NEAA non-essential amino acids
PDMS polydimethylsiloxane
ROI region of interest
RT-qPCR Real time quantitative polymerase chain reaction
$y_0$ initial phase value
$X_0$ water influx time

DETAILED DESCRIPTION

BRIEF DESCRIPTION OF THE FIGURES

FIG. 1*a*: a tessellation of squares. FIG. 1*b*: a tessellation of equilateral triangles. FIG. 1*c*: a tessellation of regular hexagons. FIG. 1*d*: an array of circular objects can be overlaid with a square tessellation. FIG. 1*e*: an array of circular objects overlaid with a tessellation of regular hexagons such that the objects are uniquely positioned within adjacent tiles. FIG. 1*f*: an array of circular objects overlaid with a tessellation of regular hexagons such that the objects are not uniquely positioned within adjacent tiles.

Figure 1:
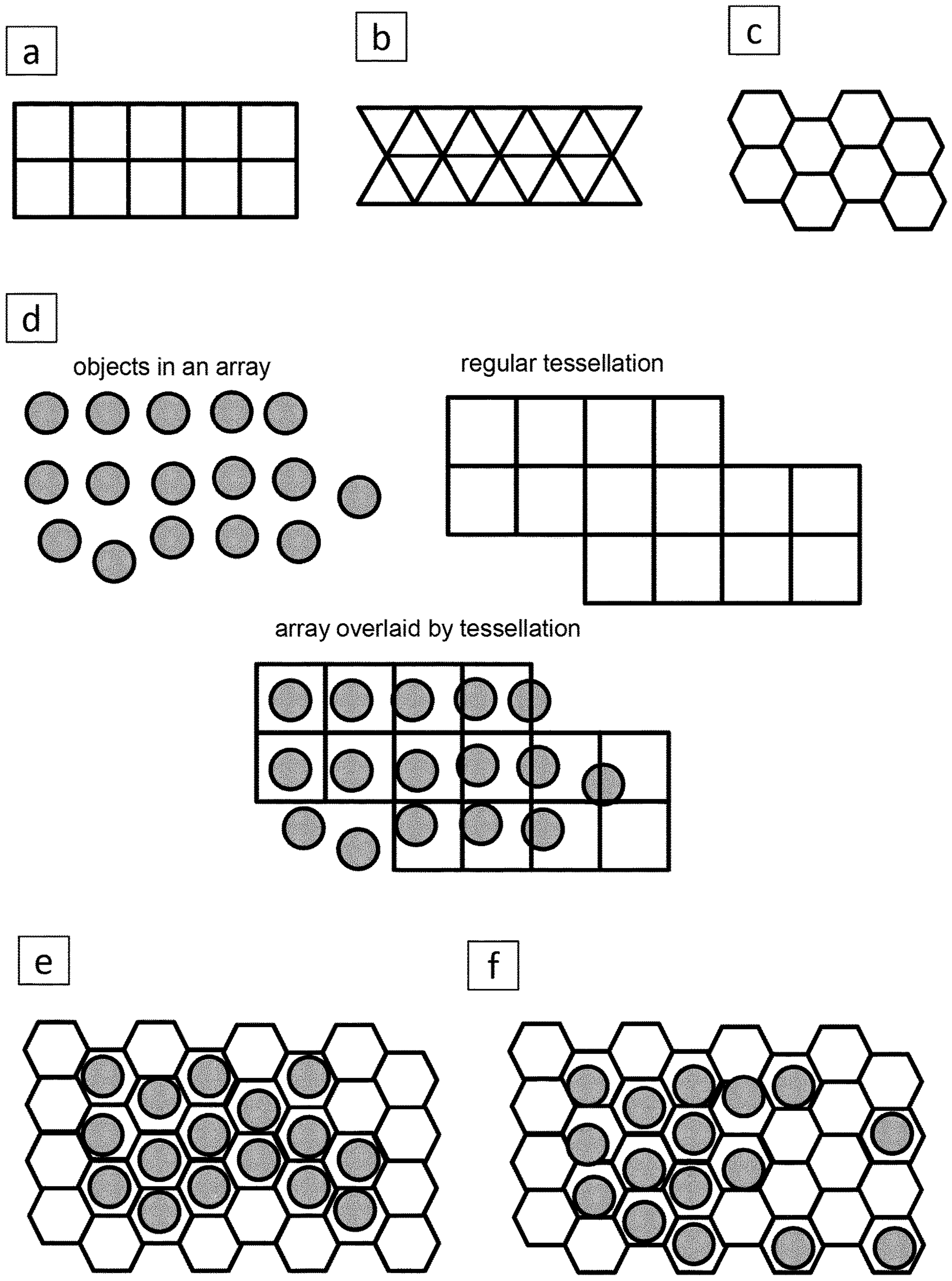
FIG. 1. Arrays and tessellations
Figure 2:
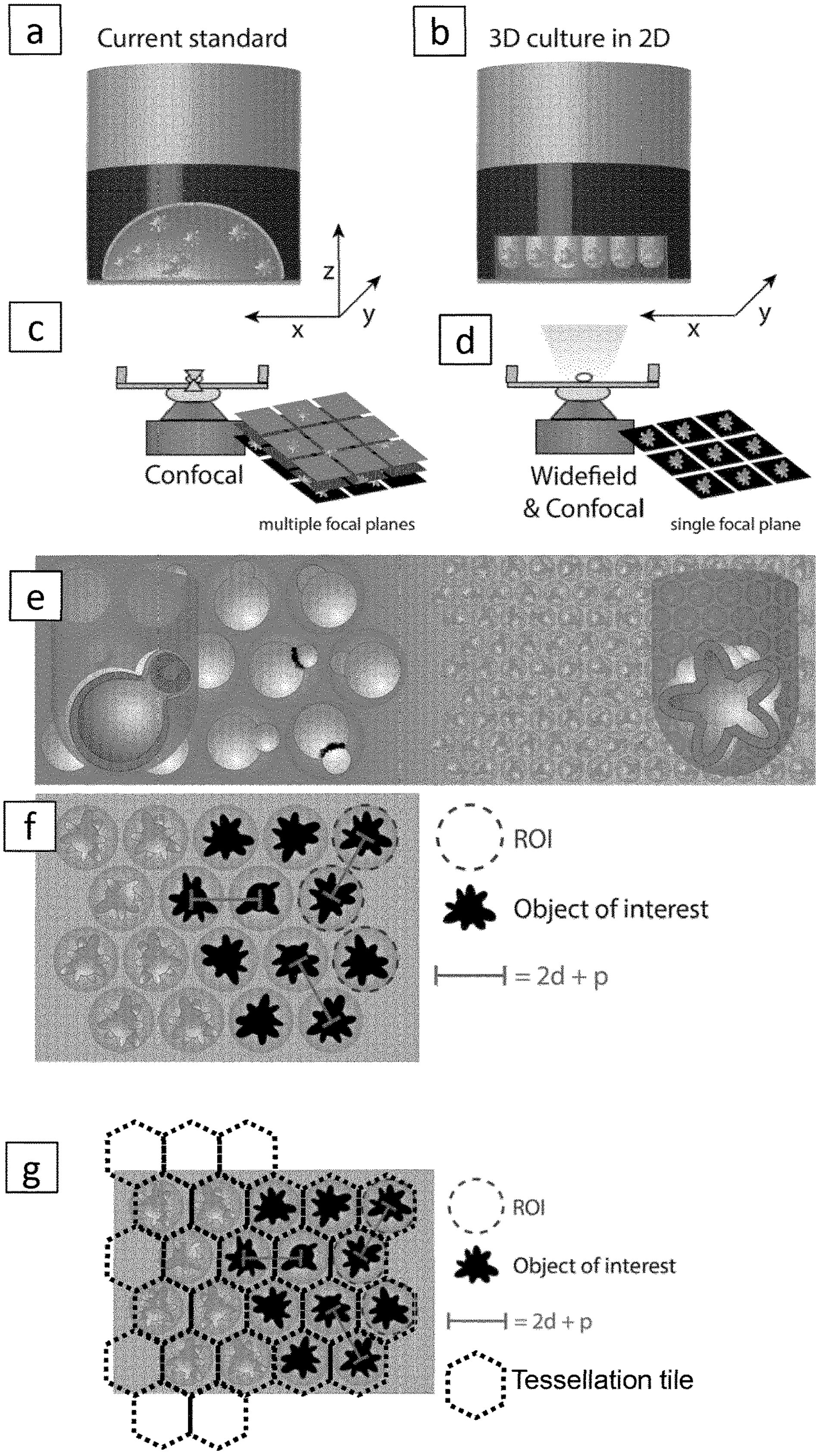
FIG. 2. A method for production of organoid arrays

A major limitation of 3D cell culture is that cellular structures are distributed over many different foci (FIG. 2*a*). The present invention provides a system for 3D culture within a single focal plane (FIG. 2*b*). 3D cell culture slows down image analysis (FIG. 2*c*), whilst culturing cells within a single focal plane eliminates the need for performing z-stacks based analysis (FIG. 2*d*). Within an array, wherein all the objects in an array can be overlaid with a tessellation of regular hexagons such that the objects are uniquely positioned within adjacent tiles, all the organoids can be localized within a single region of interest (ROI) (FIG. 1*e-g*).

Figure 3:
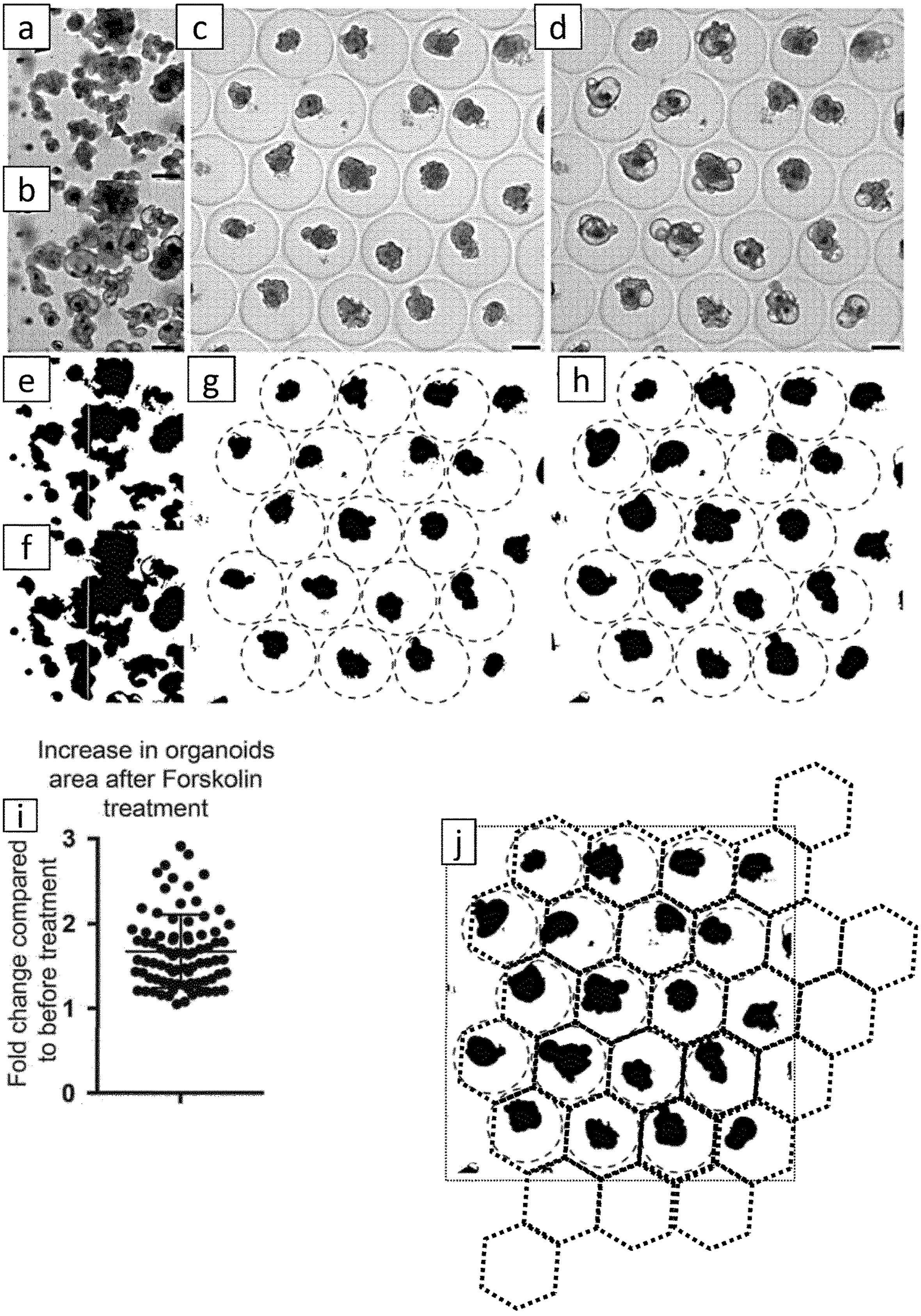

FIG. 3. Organoid arrays vs 3D Matrigel drops

Figure 4:
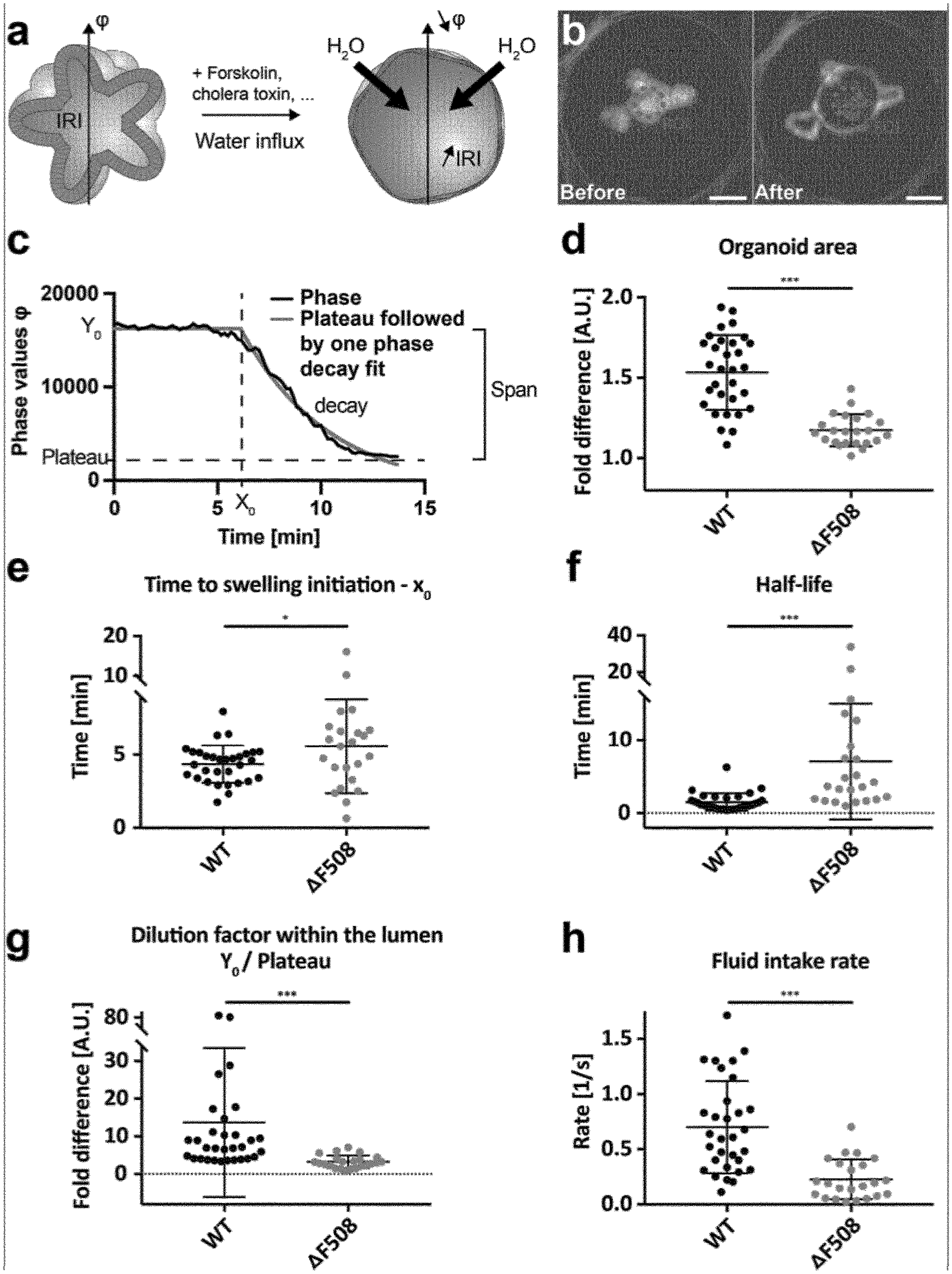

Bright field imaging of organoids grown in Matrigel drops (FIG. 3*a, b*) or organoid cultures (FIG. 3*c, d*) at a first (FIG. 3*a, c*) and second time point (FIG. 3*b, d*). Image analysis of organoids grown in Matrigel drops (FIG. 3*e, f*) or organoid cultures (FIG. 3*g, h*). FIG. 3*i*: Fold change in organoid size following Forskolin treatment of organoids grown in arrays. FIG. 3*j*: Within an array of organoids, all the organoids in the array can be overlaid with a tessellation of regular hexagons such that the organoids are uniquely positioned within adjacent tiles, FIG. 4. Use of organoid arrays in an assay of transmembrane fluid transport FIG. 4*a*: a schematic showing the treatment of an organoid with cystic fibrosis transmembrane conductance regulator (CFTR) agonists, such as Forskolin. FIG. 4*b*: the phase shift of an organoid treated with Forskolin. FIG. 4*c*: phase change over time of an organoid treated with a CFTR agonist. FIG. 4*d, e, f, g, h*: comparison of various physical responses of wild type or CFTR deletion mutant organoids treated with CFTR agonists.

Figure 5:
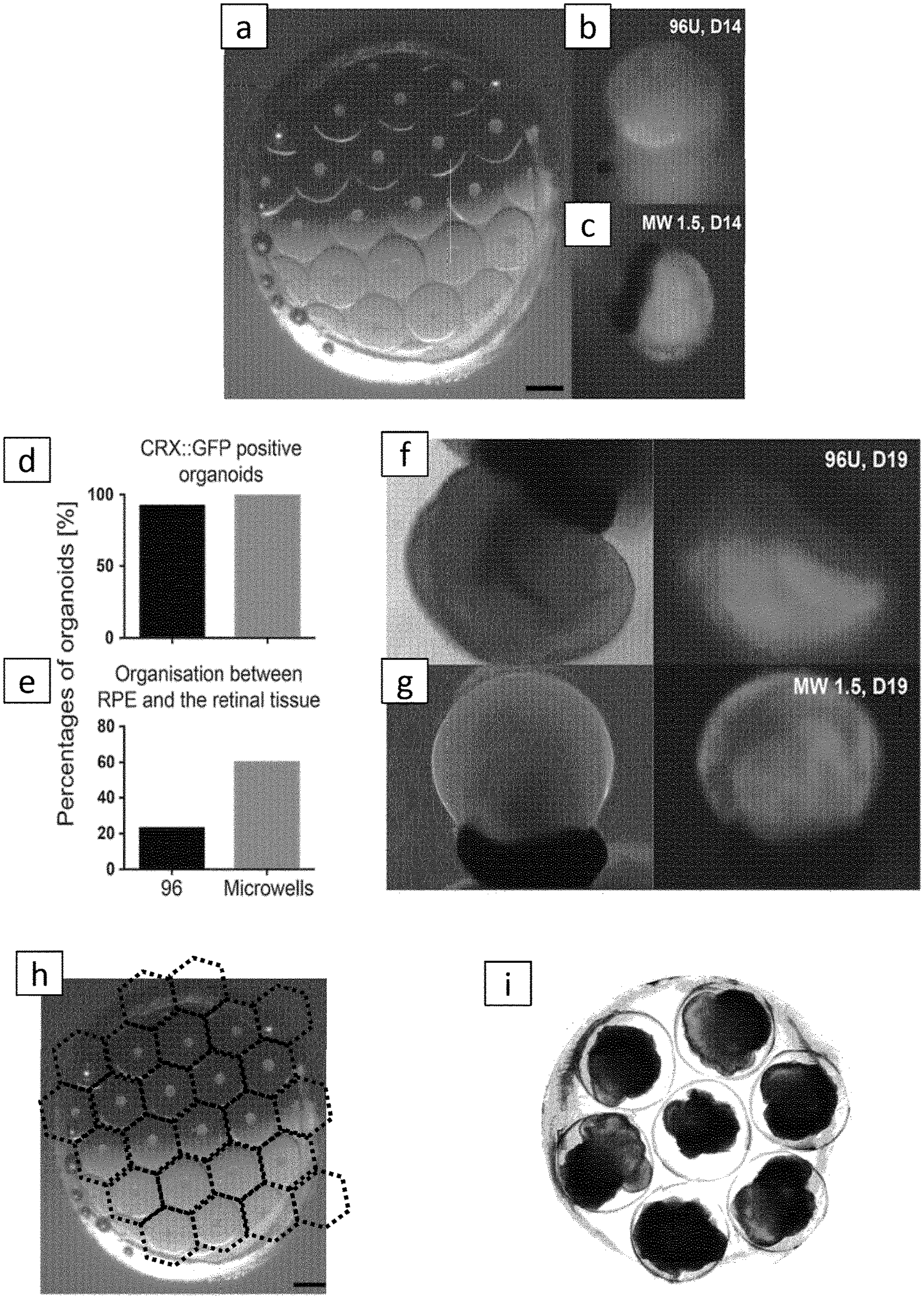

FIG. 5. Retinal organoid arrays

FIG. 5*a*: retinal organoids grow in an array. FIG. 5*c, d* Expression of CRX on 14 day retinal organoid cultures in 96 U bottom low adherent plates (96U) (FIG. 5*b*) or organoid array microwells (MVV) (FIG. 5*c*). FIG. 5*d*: quantification of CRX-GFP expression in organoids cultured in 96U bottom plates or MW. FIG. 5*e*: quantification of organization between RPE and the retinal tissue in organoids cultured in 96U bottom plates or MW. FIG. 5*f-g*: Maturation and polarity of organoids cultured in 96U bottom plates or MW. FIG. 5*h*: Within an array of retinal organoids, all the organoids in the array can be overlaid with a tessellation of regular hexagons such that the organoids are uniquely positioned within adjacent tiles, FIG. 5*i*: magnified image of retinal organoids within an array.

Figure 6:
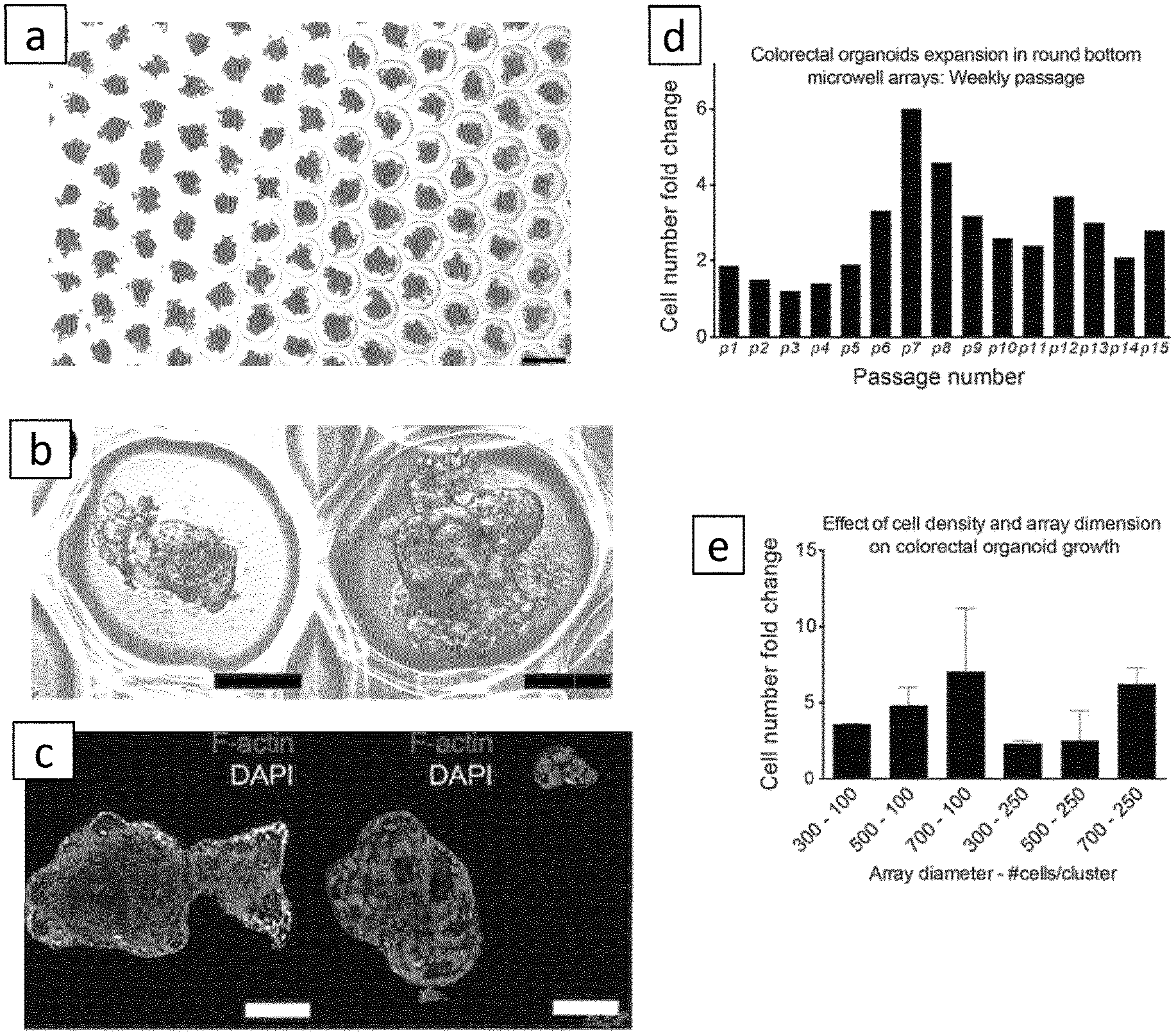

FIG. 6. Colonoid arrays

FIG. 6*a*: culture of primary colorectal tumor biopsy samples over time. FIG. 6*b*: multi-cellular aggregates (spheroids) of tumor cells. FIG. 6*c*: the polarity of tumoroids grown in arrays. FIG. 6*d*: the viability of colonoids in microwell arrays over time. FIG. 6*e*: the effect of cell density on the growth of colonoids in organoid arrays.

Figure 7:
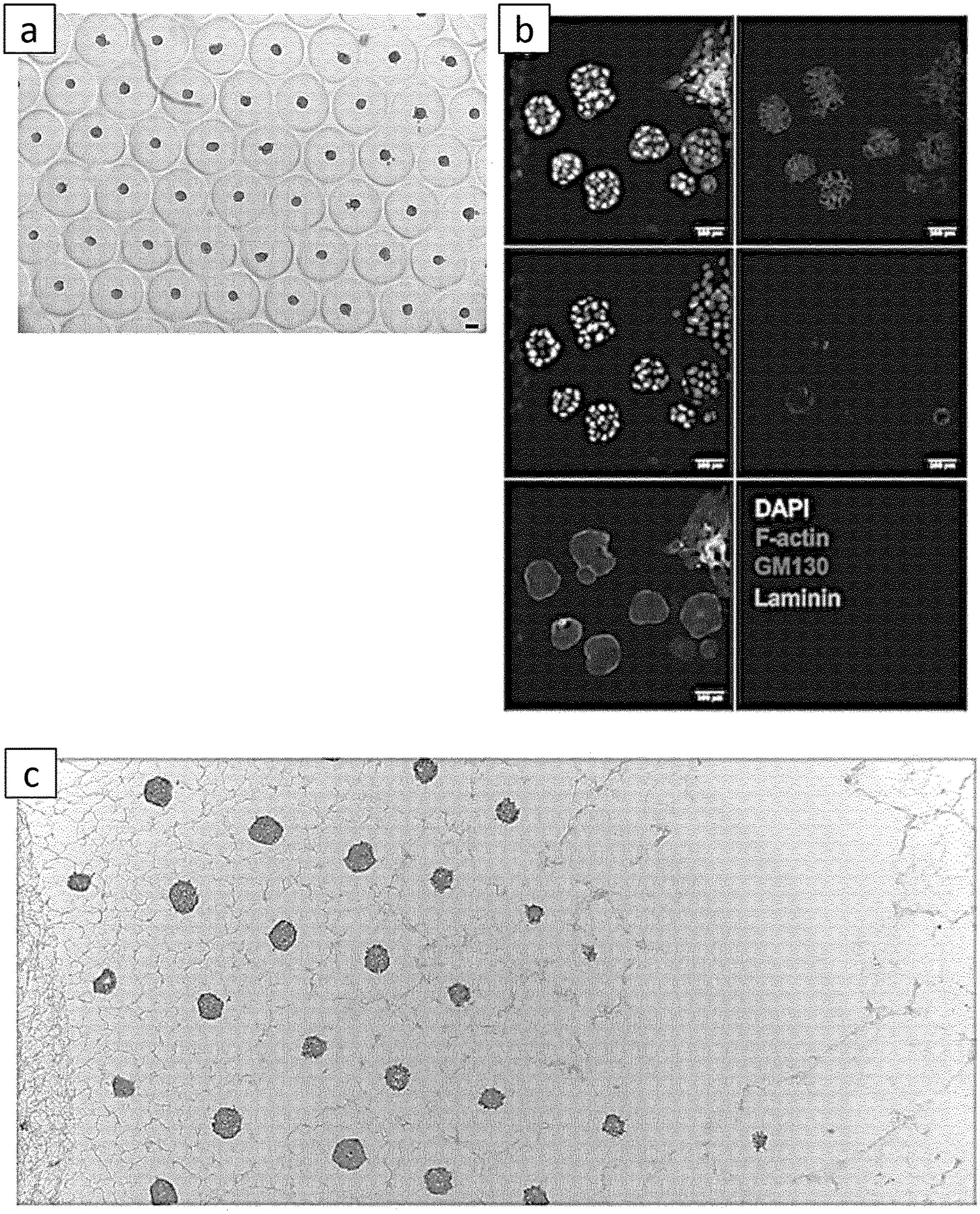

FIG. 7. Mammary gland organoid arrays

FIG. 7*a*: growth of MCF10A cells in an array. FIG. 7*b*: polarization of MCF10A colonies within an array. FIG. 7*c*: one focal plane of an MCF10A tumoroid array.

Figure 8:
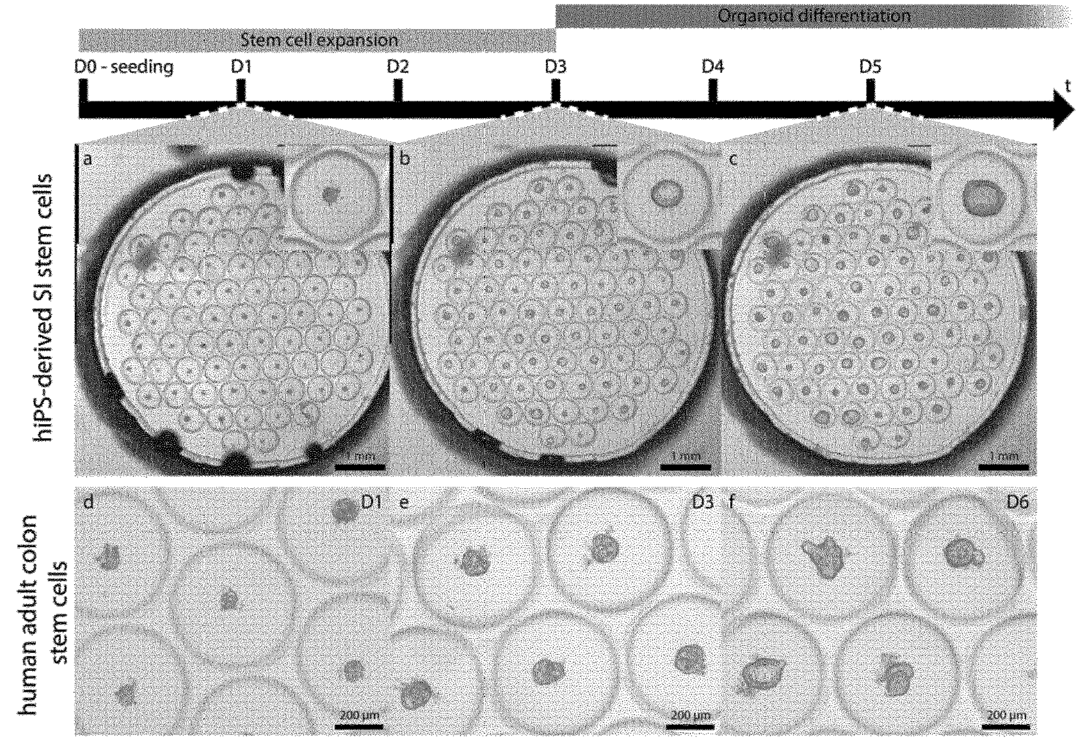

FIG. 8. Growth and differentiation of iPS-derived intestinal stem cell colonies.

FIG. 8: Generation of human iPS-derived intestinal organoid arrays and human colon organoid arrays. Cells are seeded at day 0 and form stem cell colonies after overnight incubation. (a) Representative brightfield image of an array of iPS-derived intestinal stem cell colonies. (b) Representative brightfield image of the same stem cell colonies grown for another two days in stem cell expansion medium. (c) Representative brightfield image of an array of the same colonies differentiating into human iPS-derived foregut organoid after two days of differentiation. Organoid differentiation can be prolonged on the same array until reaching a desired differentiation state. (d) Representative brightfield image of an array of human adult colon stem cell colonies. (e) Representative brightfield image of the same stem cell colonies grown for another two days in stem cell expansion medium. (f) Representative brightfield image of an array of the same colonies differentiating into human colon organoid after two days of differentiation. Organoid differentiation can be prolonged on the same array until reaching a desired differentiation state.

Figure 9:
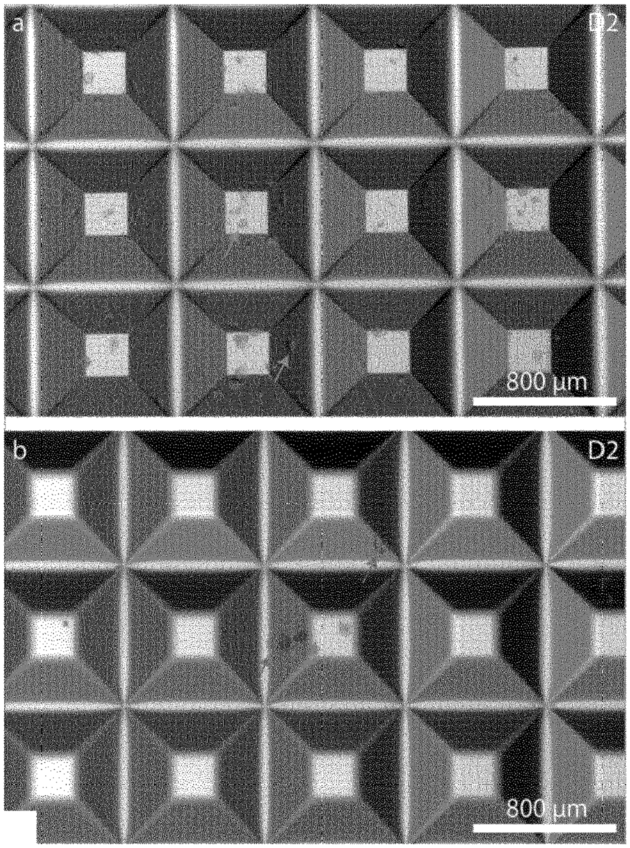

FIG. 9. Growth of mouse intestinal organoid arrays

FIG. 9: Mouse intestinal organoid arrays onto Aggrewell™ microwells after two days of stem cell expansion. (a) Mouse intestinal stem cell colonies onto uncoated Aggrewell™ microwells. (b) Mouse intestinal stem cell colonies onto coated Aggrewell™ microwells.

Figure 10:
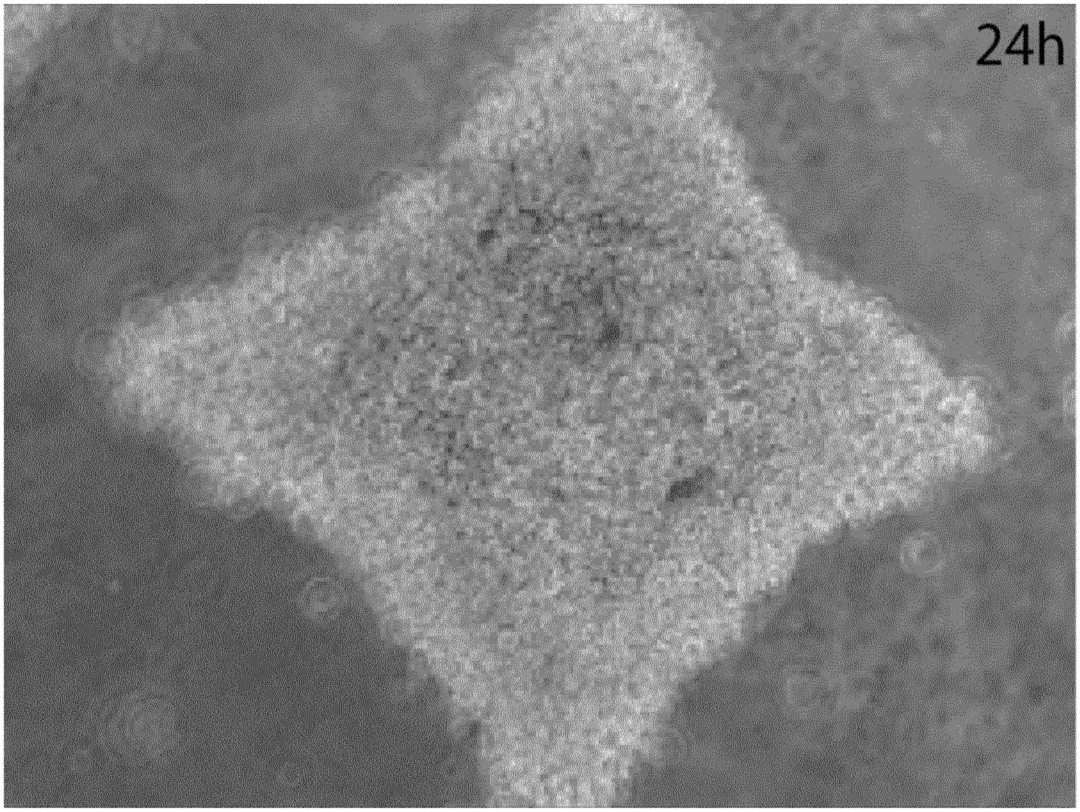

FIG. 10. Aggregration of mouse embryonic stem cells

FIG. 10: Representative image of CRX::GFP Mouse Embryonic Stem Cells aggregating into Aggrewell microwells of 800 μm in size after 24 hours.

DEFINITIONS

An array as used herein is defined as an ordered arrangement of similar or identical objects. Typically, the objects in an array can be divided into rows and columns. An array of organoids is an ordered arrangement of at least one organoid. In biology, arrays of samples or biological materials (microarrays) are used for high-throughput analysis.

Cartigel is an extracellular matrix extract of cartilage.

A biofunctional hydrogel is a hydrogel that contains bioactive (or bio-adhesive) molecules, and/or cell signaling molecules that interact with living cells to promote cell viability and a desired cellular phenotype. Biofunctional hydrogels may also be referred to as bioactive. Examples of bio-adhesive molecules include, but are not limited to, fibronectin, vitronectin, bone sialoprotein, laminin, collagen and elastin. These molecules contain cell adhesive peptides that govern their interaction with cells. Examples of cell adhesion peptide sequences include, but are not limited to, fibronectin-derived RGD, KQAGDV, REDV and PHSRN, laminin-derived YIGSR, LGTIPG, IKVAV, PDGSR, LRE, LRGDN and IKLLI, collagen-derived DGEA and GFOGER, and elastin-derived VAPG. A dilute hydrogel is defined here as a hydrogel that due to its low solid content can behave like a viscous fluid or semi-solid media, whereas a non-dilute hydrogel behaves like a typical viscoelastic gel.

Bio-active (or bio-adhesive or biofunctional) molecules are molecules that interact with cells to promote cell viability and have been previously described for a variety of cell types. Bio-adhesive molecules that render a hydrogel biofunctional include, but are not limited to, fibronectin or functional variants thereof, for example FF III1-C fragment, FNIII9-10 fragment, and FNIII12-14, or RGD containing peptides, for example RGD, RGDS, RGDSP, RGDSPK, RGDTP and RGDSPASSKP. Functional variants of bioactive molecules are molecules having the same or similar biological or biochemical function and a similar sequence or composition—for example, truncated molecules, or fragments of such molecules.

A biocompatible hydrogel is a polymer network that is not significantly toxic to living tissue and/or cells, and does not elicit an immunopathogenic response in healthy individuals. A biocompatible active mechanism is a process that is not toxic to particular cells or tissues, for example a temperature increase within the physiological temperature range of tissues, or that is applied briefly enough so as not to cause significant toxicity.

Culturing cells refers to the process of keeping cells in conditions appropriate for maintenance and/or growth, where conditions refers to, for example, the temperature, nutrient availability, atmospheric $CO_2$ content and the cell density in which the cells are kept. Cells can be cultured in vivo or in vitro. The appropriate culturing conditions for maintaining, proliferating, expanding and differentiating different types of cells are well-known and documented. The conditions suitable for organoid formation are those that facilitate or permit cell differentiation and the formation of multicellular structures. See Materials and Methods for details of culturing conditions suitable for the cells used in the examples.

A focal plane is the plane or flat surface through the focus perpendicular to the axis of a lens of, for example, of a microscope. At a particular focus, all objects in view are within the same focal plane.

High-throughput screens and assays are those which are automated to achieve levels of repeatable data acquisition unfeasible using manual methods.

A hydrogel (gel) is a 3D matrix comprising a network of hydrophilic polymer chains.

In situ is a biological term for culturing cells or tissues without moving their position.

Matrigel is a commercial product widely used in both 2D and 3D models of cell culture. It comprises a solubilized basement membrane preparation extracted from an ECM rich mouse tumour.

A microwell is a cavity capable of holding liquid, comprising an open mouth, a hollow shaft and a bottom. A microwell can also be referred to as a well, microcavity or cavity. A well is usually a well of a wellplate. Microwell plates comprise arrays of equivalent microwells. These microwells may form patterns in the substrate forming the plate, for example to form a patterned hydrogel. Microwells may be flat-bottomed, or round (U)-bottomed. The shaft of a microwell is typically cylindrical. The depth of a microwell refers to the distance from the mouth to the lowest part of the bottom.

Microchannels are fluid conduits provided within a surface. Microchannels can form microfluidic delivery networks within a hydrogel, as has been previously described (Brandenberg and Lutolf, 2016).

A multicellular stem cell containing aggregate is a population of cells containing at least one stem cell; this may also be referred to as an embryoid body.

Myogels are extracellular matrices extracted from skeletal muscle (Abberton et al., 2008).

Organoids are three-dimensional culture systems of organ-specific cell types that develop from stem cells and self-organize (or self-pattern) through cell sorting and spatially restricted lineage commitment in a manner similar to the situation in vivo. As used herein, an organoid is defined as a 3D culture of stem cells and their differentiated progeny, initiated from a single stem cell or a multicellular aggregate of cells with at least one stem cell (that is, an embryoid body). Stem cells may be isolated from tissue or organoid fragments. Organoids grown from isolated intestinal crypts or stem cells may also be referred to in the field as “enteroids” or “colonoids”. Organoids grown from or containing cancerous cells are “tumoroids”. Organoids are distinct from embryoid bodies at least in that organoids are self-organizing and thereby become architecturally similar to an in vivo tissue/organ, whereas embryoid bodies are not. Indeed, in order to obtain organoids from embryoid bodies, the embryoid body must typically be treated with patterning factors to drive the formation of the desired organoid identity.

Seeding cells refers to the process of allowing a suspension of cells to settle onto a surface through gravity or centrifugation.

The shear modulus of a hydrogel is equivalent to the modulus of rigidity, G, elastic modulus or elasticity of a hydrogel. The shear modulus is defined as the ratio of shear stress to the shear strain. The shear modulus of a hydrogel can be measured using a rheometer (Example 1, 1.4 Materials and Methods).

Stem cells are understood herein as cells capable of forming an organoid.

A tessellation is a 2D arrangement of polygons, or tiles, fitted together in a repeated pattern without gaps or overlapping. A regular tessellation is a tessellation made-up of congruent (i.e. identical) regular tiles, where the sides and angles within a regular tile are all equivalent. There are only 3 types of regular tessellation, comprising square, equilateral triangle or regular hexagonal tiles (FIG. 1*a*-*c*). Overlaying a surface with a tessellation is the process of superimposing the tessellation on to the surface, as one would overlay a reference grid. FIG. 1*d* shows an array of objects in a 2D plane overlaid with a regular tessellation. Overlaying an array with a tessellation such that the objects in the array are uniquely positioned within adjacent tiles of the tessellation, requires that each object is overlaid by its own tile (that does not overlay any other objects in the array), and that each such tile is adjacent to a tile that also uniquely overlays an object, as shown in FIG. 1*e*. An array of objects that cannot be overlaid by a regular tessellation such that the objects are not uniquely positioned within adjacent tiles of the tessellation is shown in FIG. 1*f*.

Description

In a first aspect the present invention relates to a method for making an array of organoids, comprising:

i. seeding stem cells on a surface
ii. culturing the stem cells of step i) in situ to allow their aggregation into multicellular stem cell containing aggregates
iii. culturing the multicellular stem cell aggregates of ii) in situ in conditions suitable for organoid development, wherein the array of organoids is within a single focal plane and the surface may be overlaid with a regular tessellation, such that the organoids are uniquely positioned within adjacent tiles of the tessellation.

In preferred embodiments, the surface is a hydrogel; more preferably a biofunctional hydrogel. The hydrogel is preferably non-dilute; and may form a gel with a stiffness (shear or elastic modulus) between about 150 Pa and about 50 kPa.

The invention solves the problem of providing a reproducible method for producing organoid arrays in situ that can be subjected to high-throughput and real-time image analysis. The organoid arrays produced by this method possess such a degree of geometrical homogeneity that each organoid in the array can be independently imaged and tracked over time in high-throughput, without the need for extensive image analysis. Furthermore, the organoid arrays of the present invention develop from an array of stem cells in situ, providing for the first time a novel method for investigating factors effecting organoid development in high throughput.

In another aspect the invention additionally comprises overlaying the multicellular aggregate with an overlay, preferably wherein the overlay comprises a cell compatible material, more preferably wherein the cell compatible material is a hydrogel. The hydrogel of the overlay may be dilute such that it forms a viscous solution or semi-solid media, or may form a gel with a stiffness (shear or elastic modulus) between about 150 Pa and about 50 kPa.

The stiffness of the hydrogel substrate of the bottom (i.e. surface) and the upper (i.e. overlay) layers controls the growth and morphogenesis of the stem cell and organoid arrays. Different types of organoid may prefer hydrogels with different stiffness values. Optic Cup organoids, for example, typically require stiffer substrates that promote differentiation of stem cells in the retinal tissue lineage.

In one aspect of the invention, the surface is imprinted with cavities or microwells of various sizes, shapes and depths. The arrays of the invention may be formed by taking a suspension of single stem cells, adjusting the density to reach an accurate or appropriate number of cells per cavity and depositing this cell suspension on top of the patterned hydrogel surface in order to let the cells distribute in each of the cavities or microwells by gravity or centrifuge. The density of the cavities is so high that every cell ends up in a cavity. After 15-30 minutes in the incubator the cells are all gathered at the bottom of the cavities, such there are not gaps in the tessellating pattern of occupied microwells. Extra media can be added to the container where the patterned hydrogel layer was deposited such that the cells remain undisturbed at the bottom of the cavities. The cells compact into multicellular aggregates with an unlimited upper limit number of cells, of which at least one is a stem cell, preferably starting from a homogeneous population of stem cells. The stem cell aggregates or compacting structures may be overlaid, as noted above, preferably with a dilute or non-dilute hydrogel, to promote the development of organoids. This forms a new type of sandwich culture. Finally, appropriate media, and the combinations of nutrients and proteins, such as growth factors and morphogens, are added to the culture homogenously to guide the growth and development of the organoids.

The hydrogel of either the surface or the overlay or both is preferably formed of naturally derived biomaterials such as polysaccharides, gelatinous proteins, or ECM components comprising the following or functional variants thereof: agarose; alginate; chitosan; dextran; gelatin; laminins; collagens; hyaluronan; fibrin, and mixtures thereof. Alternatively the hydrogel may be formed of Matrigel, Myogel and Cartigel, or a combination of Matrigel, Myogel and Cartigel and a naturally derived biomaterial or biomaterials.

The proteins used in the present invention may be naturally derived or recombinant.

The hydrogel of either the surface or overlay or both may be a macromolecule of hydrophilic polymers that are linear or branched, preferably wherein the polymers are synthetic, more preferably wherein the polymers are poly(ethylene glycol) molecules and most preferably wherein the poly (ethylene glycol) molecules are selected from the group comprising: poly(ethylene glycol), polyaliphatic polyurethanes, polyether polyurethanes, polyester polyurethanes, polyethylene copolymers, polyamides, polyvinyl alcohols, poly(ethylene oxide), polypropylene oxide, polyethylene glycol, polypropylene glycol, polytetramethylene oxide, polyvinyl pyrrolidone, polyacrylamide, poly(hydroxy ethyl acrylate), poly(hydroxyethyl methacrylate) and mixtures thereof.

In another aspect of the invention the surface comprises an array of microwells, wherein each microwell in the array is cable of supporting:

i. aggregation of defined numbers of stem cells into a multicellular aggregate of reproducible size and shape,
ii. spatially confined cell expansion, and/or
iii. self-organization of stem cells and organoid development.

The microwell may function to restrict movement of a developing organoid such that the centre of mass of the organoid is less than about 100 μm from the centre of the bottom of the microwell, i.e. within sufficient distance of the centre of the bottom of the microwell to facilitate high-throughput processing of the array. The microwells are also preferably round (U)-bottomed.

The microwells may have a diameter of about 10 μm to about 5 mm, a curvature radius of about 5 μm to about 2.5 mm, and a depth of about 10 μm to about 6 mm. Preferably the depth of the microwells is 1.2 times the diameter of the cavity. The dimensions and shape of the microwells or cavities have an effect on controlling the growth and morphogenesis of organoids.

The surface used in the method of the invention may comprise one or more bioactive factors that promote stem cell expansion, differentiation, self-organization and/or organoid development, so as to maintain, promote and/or direct growth and morphogenesis of the developing stem cells and/or organoids. The bioactive factors are preferably extracellular matrix factors or proteins of major signalling pathways, more preferably proteoglycans, non-proteoglycan polysaccharide or fibrous proteins. The biofactors may be provided on the surface of each microwell, and preferably delivered to each microwell by passive diffusion from microcavities in the surface. The microcavities may form reservoirs or channels within the surface and may be positioned within the surface on either or on both sides of each microwell.

In particular, the patterned hydrogel or surface of the invention may be interfaced with a biocompatible hard material such as plastic or a soft polymer such as PDMS (polydimethylsiloxane) that form microfluidic networks or reservoirs. These microfluidic networks or the reservoirs can be the delivering source/sink or can be interfaced with the hydrogel to allow microfluidic fabrication in the gel phase to create the delivering source/sink to the cavities (Brandenberg and Lutolf, 2016). The microfluidic networks can be actuated (i.e. for convective flow) or the molecules can be delivered passively by diffusion, by a gradient that may span 1 or more microcavities or microwells. The microfluidic networks or reservoirs can be below the microcavities or on either or on both sides of the microcavities.

Establishment of the local delivery or the gradient of the molecules of interest may be established by control of the local concentration of the molecules inside the networks. The molecules may diffuse in the hydrogel space between the microfluidic networks or reservoirs and the microcavities, such that molecules' movement is driven solely by diffusion. The diffusion time depends on the molecular weight of the molecules of interest and the distance between the microfluidic networks or reservoirs and the microcavities.

In another aspect the invention relates to an array of organoids produced by the methods of the invention.

In yet another aspect the invention relates to an array of organoids on a surface, wherein i) the array of organoids has been grown in situ on the surface from an array of stem cells or from an array of multicellular aggregates, wherein each aggregate comprises at least one stem cell,
ii) the array of organoids is within a single focal plane,
iii) the surface may be divided by a regular tessellation such that the organoids are individually positioned within adjacent tiles of the tessellation.

The surface is a hydrogel, preferably a biofunctional hydrogel.

Preferably, the array of organoids of the invention is formed in situ on the surface from an array of stem cells or from an array of homogenous stem cell populations.

In another embodiment the density of organoids in the array is at least one organoid per $cm^2$, preferably at least 30 organoids per $cm^2$, more preferably at least 1 million organoids/$cm^2$, most preferably 1.1 million organoids per $cm^2$, more preferably wherein the centre of mass of each organoid in the array is about 100 μm or less from the centre of the tile in which it is positioned, In another embodiment the centre of mass of each organoid in the array is about 100 μm or less from the centre of the tile in which it is positioned, preferably wherein the distance between the centre of mass of adjacent organoids in the array is from about 10 to about 5000 μm, preferably 10 to about 2000 μm, such that the array is suitable for high-throughput processing and imaging.

The array of the invention may be positioned in a well of a multi-well plate, preferably wherein the plate is compatible with liquid handling, automated liquid handling, high throughput screening and/or micro-pipetting, more preferably wherein the wells of the plate are flat-bottomed.

In another aspect the invention relates to a kit comprising a surface of the invention and may also comprise media for culturing stem cells in cell survival conditions, media for culturing cells in differentiation and organoid formation conditions, and preferably stem cells. The media components are preferably provided in a separated vessel, more preferably a tube or a bottle. The stem cells are also preferably provided in a separated vessel, preferably a tube or cryotube.

In another aspect the invention comprises the kit for making an array of organoids according to the invention, comprising i) an array of microwells or cavities imprinted into a surface according to the invention;
ii) a defined medium, comprising tissue specific factors, nutrients and morphogens; and
iii) stem cells and/or differentiated cells.

Preferably the surface is provided in a culture container, the media components are provided in a separated vessel, preferably a tube or a bottle, and the stem cells are provided in a separated vessel, in a tube, or in a cryotube. Preferably, the array is provided pre-supplied in a container, preferably in wells of a multi-well plate, of a microtiter plate or in a transwell of a multi-well plate, in an already reacted form, immersed in liquid. The medium may be provided pre-supplied in a container, preferably in a bottle, a tube or in a multitude of ready-to-mix bottles and tubes, if possible at a low temperature. The cells are preferably provided in a container, preferably a cryotube, and at very low temperatures if possible.

In another aspect the invention relates to a screening assay for quantitatively assessing organoid development, or perturbations thereof, comprising:

i. seeding a stem cell population into a micro-structured cell culture substrate triggering their aggregation into multicellular spheroids,
ii. applying pharmacologic compounds, biomolecules, or cells (i.e. drug substance) to the array of stem cell colonies,
iii. promoting organoid development by provision of instructive signals for self-renewal, differentiation and/or morphogenesis,
iv. monitoring of an effect of a pharmacologic compounds, biomolecules, or cells (i.e. drug substance) on organoid size, shape, cellular composition,
v. changing medium regularly on top of the organoid array without disturbing location of organoids to allow growth periods of 1 week to several months.

Preferably, the perturbations are introduced locally in the culture using microfluidic networks or reservoirs.

In another aspect the invention relates to an organoid-based screening assay, comprising i. culturing a stem cell population into an array of organoids,
ii. applying pharmacologic compounds, biomolecules, or cells, to the organoid array,
iii. monitoring of an effect of the substance on the size of the organoid, its shape, its cellular composition and its phenotypic changes,
iv. analysing the phenotypic changes by widefield or brightfield imaging,
v. monitoring of an effect of the substance on the variations of specific markers (reporter) levels of interest by imaging,
vi. analysing the level of the markers by widefield fluorescence imaging and confocal microscopy
vii. optionally analysing the level of the markers by gene expression analysis
viii. optionally analysing the level of non-reporter molecules by immunofluorescence
ix. optionally analysing the cellular ultrastructures by electron microscopy
x. optionally analysing the level of protein markers by proteomics.

In this, and in each of the following assays described herein, preferably the organoid array is formed according to the methods described herein.

In another aspect the invention relates to an organoid-based screening assay for personalized medicine, the assay comprising i. providing a tissue biopsy sample from a patient,
ii. growing stem cells or tumour cells isolated from the biopsy sample as an array of organoids,
iii. culturing the organoid array under suitable conditions in the presence of the pharmacologic compounds or biomolecules to be tested, and
iv. monitoring the successful reduction in cell damage or death, restoration of epithelial junction integrity or inflammation,
v. optionally monitoring the successful targeting of the metastatic and tumorigenic cells In another aspect the invention relates to an organoid-based screening assay for personalized medicine, the assay comprising i. providing a tissue biopsy sample from a patient,
ii. generating induced pluripotent stem cells from the biopsy,
iii. optionally modifying specific gene sequences onto the generated induced pluripotent stem cells using, for example but not limited to, CRISPR technology,
iv. growing the induced pluripotent stem cells generated from the biopsy sample as an array of organoids,
v. culturing the organoid array under suitable conditions in the presence of the pharmacologic compounds or biomolecules to be tested, and
vi. monitoring the successful reduction in cell damage or death, restoration of epithelial junction integrity or inflammation,
vii. optionally monitoring the successful targeting of the metastatic and tumorigenic cells,
viii. defining the appropriate treatment for specific diseases or healthy tissue of which the phenotype had been reproduced in vitro.

In another aspect the invention relates an organoid-based screening assay for personalized medicine or for compound screening of transepithelial transport using holographic microscopy, the assay comprising i. providing a tissue biopsy or induced pluripotent derived stem cells,
ii. growing stem cells or tumour cells isolated from the biopsy sample as an array of epithelial organoids,
iii. mature the epithelial organoids on array,
iv. induce luminal dilution or intracellular dilution by stimulating the organoids using ion transport channel activators (such as forskolin and cholera toxin),
v. monitoring the dilution by tracking the decrease in refractive index by imaging using holographic microscopy,
vi. optionally defining the compound hit treatment for specific diseases or healthy tissue of which the phenotype had been reproduced in vitro.

vii. optionally defining the best treatment combination for specific diseases or healthy tissue of which the phenotype had been reproduced in vitro.

EXAMPLES

Those skilled in the art will appreciate that the invention described herein is susceptible to variations and modifications other than those specifically described. It is to be understood that the invention includes all such variations and modifications without departing from the spirit or essential characteristics thereof. The invention also includes all of the steps, features, compositions and compounds referred to or indicated in this specification, individually or collectively, and any and all combinations or any two or more of steps or features. The present disclosure is therefore to be considered as in all aspects illustrated and not restrictive, the scope of the invention being indicated by the appended claims, and all changes which come within the meaning and range of equivalency are intended to be embraced therein.

The foregoing descriptions will be more fully understood with reference to the following Examples. Such Examples, are, however, exemplary of methods of practicing the present invention and are not intended to limit the scope of the invention.

Example 1. Organoid Arrays: Characteristics and Analysis 1.1. Introduction

Using the platform device described in WO2016103002 A1 (Höhnel et al., 2016) the inventors generated arrays of organoids in high throughput.

1.2. Results

A hydrogel layer was imprinted with cavities or microwells of various size/shape/depth as described in WO2016103002 A1 (Höhnel et al., 2016) and used to prepare arrays of organoids. The organoids were grown in situ, such that from initiation to formation of the final organoid structure, there was no transfer to pre-formed structures to another position or culture environment. The dimensions of the cavities were adjusted according to type of organoid array to be prepared (Table 1).

TABLE 1

Summary of various array applications and their corresponding microwell geometry

| Array | Microwell diameter (μm) | Microwell height (μm) | Distance between microwells (μm) | Microwell array diameter (μm) |
|---|---|---|---|---|
| Spheroids | 400 | 480 | 40 | 10 |
| Intestinal organoids | 500 | 600 | 40 | 6 |
| Retinal organoids | 1500 | 1800 | 100 | 5.5 |
| Colorectal cancer organoids | 300 | 360 | 40 | 6 |
| MCF10a acini organoid | 500 | 600 | 40 | 6 |

In brief, an array of organoids was formed by taking a suspension of single stem cells, adjusting the density to reach the accurate number of cell per cavity, depositing this cell suspension on top of the patterned hydrogel surface and letting the cells distribute in each cavity by gravity or centrifuge. The density of the cavities was so high that every cell ended up in a cavity. After 15-30 minutes incubation the cells were all gathered at the bottom of the cavities. Extra media could be added to the container where the patterned hydrogel layer was deposited without disturbing the cells at the bottom of the cavities.

The cells compacted into multicellular aggregates, starting from at least one or two cells with an upper limit number of cells that is unlimited, of which at least one is a stem cell, ideally starting from a homogeneous population of stem cells.

Optionally, the stem cell aggregates or compacting structures are overlaid with a hydrogel, that can be dilute (i.e. forms a viscous solution, or semi-solid media) or not (forms a solid gel), to promote the development of our organoids. Dilute meaning it doesn't polymerize, non-dilute means it will form a top-layer of gel.

The appropriate media, combinations of nutrients and proteins (i.e. growth factors, morphogens) are added in the culture homogenously to guide the growth and the development of the organoids.

Details of the various organoid arrays that may be formed are provided in the following Examples 2-5.

1.3. Discussion

The extremely precise repeatability of the device geometries of the organoid arrays of the present invention finally ensures the compatibility of these arrays of organoids for high throughput drug screening. Using this technology, all organoids are in one focal plane (FIG. 2*a*). This solves one of the major current limitations of 3D cell culture where image analysis is significantly slowed down due to the distribution of cellular structures over many different foci, eliminating thus the need for performing z-stacks based analysis (FIG. 2*b*). Additionally, all organoids are located within localized regions (regions of interest, ROIs), represented by the microwells (FIG. 2*f*). This particularity ensures that each organoid can be tracked and analyzed separately and over time. This gives the opportunity to assess variation on organoid populations and statistical understanding of the overall behaviors. The distances between the ROIs follow the well geometry, i.e. the distances of each ROIs will always be (2*D)+p, where D is the diameter of a particular structure, and p the inter-microwell distance. In particular, the array of organoids can be overlaid by a regular tessellation, such that the organoids are uniquely positioned within adjacent tiles of the tessellation (FIG. 2*g*). This highly reproducible pattern enables the automation of analysis and thus the compatibility of these cultures with high throughput screening.

Various analysis methods are possible on these organoid arrays. The base or surface of the device is made of a transparent biocompatible material, ensuring full optical transparency. This enables assay development based on scanning arrays using bright field live-cell tracking fluorescence and immunofluorescence (FIG. 2*d*). Using these techniques, fully comprehensive phenotypic screenings can be performed and analyzed based on ROIs for the detection of organoids.

This platform also enables for the first time the development of high-throughput histology. Due to the constant height, and geometries of the cultures, histological sectioning can be performed reproducibly, and as all aggregates as well as organoids lie on the same focal plane, the sections contain all structures in a single histological slice.

1.4. Materials and Methods 1.4.1. Fabrication of U-Bottom Microwell Arrays using PDMS Molds U-shaped micro-cavities of any size between 10 μm and 1.5 mm were generated onto standard 4 inches silicon wafers using standard Si Bosch in combination with soft lithography processes. PDMS (ratio 1:10) was poured onto the wafers and cured overnight at 75° C. After crosslinking, the PDMS stamps were demolded and punched with various diameters: 5.5, 6, 8, 10 or 12 mm.

1.4.2. Imprinting the U-Shaped Microwells onto Hydrogel Substrates

The desired stamps were mounted on the epoxy holders. The uncrosslinked PEG hydrogel mixture was deposited onto the PDMS stamp, and the holder-stamp-hydrogel construct was placed into a PDMS ring at the bottom of wells of a 24 well plate. The hydrogels were incubated at 37° C. and 5% $CO_2$ for 15 minutes to 1 h, depending on the type of hydrogel used. After crosslinking, aqueous buffer (e.g. 1×PBS) was pipetted into the wells and the holders-stamps were removed carefully. The resulting microwell arrays were sterilized thoroughly in buffer under UV light and stored at 4° C. upon use.

1.4.3. Preparation of Hydrogels

PEG hydrogels crosslinked via Michael-type addition reaction (termed 'MT-gel') were prepared as described (Gobaa et al., 2011), mixing aqueous solutions containing thiol- and vinylsulfone-functionalized 4arm- and 8arm-PEG macromers (molecular weights 10 kDa and 40 kDa, respectively) at various concentrations to adjust stiffness and stoichiometric ratio. The solution was deposited and molded as explained above. The construct was crosslinked for 15 minutes at room temperature.

PEG hydrogels crosslinked via the transglutaminase factor XIIIa (FXIIIa) (termed TG-ger) were prepared as previously described (Ehrbar et al., 2007a, 2007b, 2011). Briefly, 8arm-PEG macromers (40 kDa) bearing lysine-containing or glutamine-containing FXIIIa substrate peptides were mixed at various concentrations to adjust stiffness and stoichiometric ratio. Additionally, proteins or peptides were incorporated, covalently or non-covalently in the hydrogel network. The solution was deposited and molded as above-mentioned. The construct was crosslinked for 30 minutes at at 37° C. and 5% $CO_2$.

1.4.4. Preparation of Spheroid Microwell Arrays

Cells of interest were detached with trypsin (TrypLE, Life Technologies). Cell suspensions with specific densities were prepared (e.g. $4.68\times10^6$ cells/mL, $9.36\times10^4$ cells/mL, and 9360 cells/mL for achieving 500 cells/microwell, 100 cells/microwell and 1 cell/microwell, respectively) in the cell-type specific media. Subsequently, 50 μL of the prepared cell solution was added in the inner ring containing the microwell arrays. Cells settled down by gravitational sedimentation for 30 minutes at 37° C. and 5% $CO_2$ and 700 μL of appropriate media were then added. All cell types were cultured for 5 days and their respective media was changed every other day.

1.4.5. Mechanical Characterization of PEG Hydrogels

The shear modulus of the PEG gels was determined by performing small-strain oscillatory shear measurements on a Bohlin CVO 120 rheometer. Briefly, preformed hydrogel discs 1-1.4 mm in thickness were allowed to swell in complete cell culture medium for at least 3 h, and were subsequently sandwiched between the parallel plates of the rheometer. The mechanical response of the gels was recorded by performing frequency sweep (0.1-10 Hz) measurements in constant strain (0.05) mode, at 37° C.

Example 2. Primary Adult ISC Organoid Arrays 2.1. Introduction

As a first proof of concept, the inventors demonstrated the ease of performing and analyzing phenotypic screens using intestinal stem cell (ISCs) derived organoids and brightfield imaging. Adult ISCs are conventionally cultured in 3D Matrigel™ drops. These drops are highly variable in terms of number of organoid per culture, sizes and shapes of organoids (FIG. 3*a*). The cellular structures in Matrigel can only be analyzed manually and as single entities. This is currently a major limitation of the system. Previous studies have also evaluated organoid growth in these cultures by calculating the total combined area of all the organoids in a culture, as opposed to measuring organoids individually (Dekkers et al., 2013). Here, the inventors report the formation of intestinal organoids in U-bottom microwell arrays in a specific geometrical configuration (FIG. 3*c,d*).

2.2. Results

Previously reported studies showed that functional assays can be performed on intestinal organoids. In the scope of cystic fibrosis, a disease touching fluid transport through the intestinal epithelium, it was demonstrated that organoids derived from healthy and diseased patients react differently to an activator of this fluid transport, called forskolin (Dekkers et al., 2013). It was shown that the healthy organoids swelled more than the diseased ones. In addition, the phenotype of the diseased organoids could be rescued using combinations of drugs currently in clinical trials. However, this analysis was based on the overall surface increase of all the organoids in single culture (FIG. 3*b*). This method has major drawbacks in terms of understanding the dynamics of the individual organoids, particularly given that population effects can be masked by these averages (FIG. 3*e,f*). The method also requires the organoids to be treated with fluorescent labeling dyes to quantify the differences in average area.

The method of the present invention solves these issues. The organoid array of the invention can be used to track single organoids in specific ROIs (dotted circles) and perform area differences analysis on single organoids over time (FIG. 3*g,h*). Such an analysis reveals substantial behavioral variations between single organoids of the same population that can be tracked precisely over time (FIG. 3*i*). The array of organoids can be overlaid by a regular tessellation, such that the organoids are uniquely positioned within adjacent tiles of the tessellation (FIG. 3*j*).

The organoid array of the invention can also be used in sensitive assays of trans-membrane fluid transport in intestinal organoids. Using digital holographic microscopy (DHM), the dry mass accumulated in the lumen of the organoid can be measured by a phase shift between a reference light beam and a light beam crossing the organoid (Jourdain et al., 2014). When organoids are treated with forskolin or other CFTR agonists, fluid enters the organoid lumen, the phase shift decreases, thus the integrated performance of all the CFTR transporters (FIG. 4*a,b*).

The phase change was monitored over time and could be fitted to a plateau followed by an exponential decay with high fidelity. This fit enabled extraction of critical parameters such as the initial phase value (before the organoid reacted to the transporter agonists), $Y_0$, the final plateau, the decay, from which the half-life can be calculated, the water influx time ($X_0$) and the span (FIG. 4*c*). With these parameters, the lumen dilution factor ($Y_0$ divided by the Plateau) could be calculated which demonstrated that the amount of liquid uptake in the lumen was significantly higher in wild-type organoids than in CFTR del 508 organoids (FIGS. 4*d* to 4*h*).

2.3. Discussion

Using this assay, the inventors show that the performances of membrane transporters in intestinal organoids can be reliably evaluated. The assay can also be used to screen for optimal drug combinations for recovering the function of mutated transmembrane proteins such as the CFTR transporter.

Overall, this gives specific examples showing the ease of performing functional analysis on intestinal organoids using simple labeling-free techniques.

2.4. Materials and Methods 2.4.1. Cell Culture

LGR5::GFP mouse Intestinal Stem Cells: Crypts were extracted from murine small intestine as reported previously (Sato et al., 2009). The isolated crypts were maintained and expanded in Matrigel™, in self-renewal medium, ENR-CV (Yin et al., 2014).

2.4.2. Preparation of Intestinal Organoid Microwell Arrays

LGR5::GFP intestinal organoids were released from Matrigel™ in cold basal medium (advanced DMEM/F-12 containing 1 mM HEPES, Glutamax™ and 1% P/S). The organoids were spun down at 800 rpm, for 4 minutes, at 4° C. and resuspended in 1 mL of cell dissociation solution (TrypLE, 2 mg/mL DNAse I, Gibco, 1 mM N-acetylcysteine and 10 μM Y27632). Cells were dissociated for 8 minutes at 37° C. and subsequently washed with basal medium containing 10% fetal bovine serum (FBS, heat inactivated, Gibco). After centrifugation at 1000 rpm, for 4 minutes, at 4° C., the cells were resuspended at a density of $2.24\times10^5$ cells/mL in ENR-CV medium supplemented with 2.5 μM Thiazovivin and different concentration of laminin or Matrigel™ (see Table 3.1) in order to deposit 100 cells per microwell. 50 μL of the cell suspension was added in each microwell. The cells were aggregated overnight in medium containing a dilute non-gelling basal lamina component and subsequently sandwiched in 300 Pa non-degradable TG-PEG, containing 100 μg/mL full length laminin (Laminin Mouse Protein, Natural, ThermoFisher Scientific) and 1 mM RGD tethered to the hydrogel network. The hydrogel was left to crosslink for 4 h at 37° C. and 5% $CO_2$. Finally, 750 μL of self-renewal medium (ENR-CV) was added to each well. The aggregated mISCs were expanded in self-renewal conditions for 2 days, and the organoids were differentiated for 4 days in differentiation medium (ENR). Growth factors were replenished every other day.

Example 3. ESCs or iPSCs Derived Retinal Organoid Arrays 3.1. Introduction

Retinal organoids derived from embryonic (ESC) or induced pluripotent stem cells (IPSCs) have been shown as a potent source of progenitor cells of the retina that have a wide application, ranging from transplantation to drug screening. However, to date, no platform has been described that can reproducibly allow the high throughput generation of these retinal organoids. To this end, the inventors defined specific geometries and mechanical properties to allow the appropriate growth of mouse retinal tissue according to the methods of the invention.

3.2. Results and Discussion

In contrast with the conventional method, i.e. 96U bottom low adherent plates, a multitude of retinal organoids could be cultured in a single microwell or cavity of the surface (FIG. 5*a*). The retinal organoids were located in the center of each microwell and occupied every well of the array.

The retinal organoid structures generated on the microwell platform also showed very similar development compared to the standard culture methods. In particular, CRX, a photoreceptor precursor marker, was expressed after fourteen days of culture (FIG. 5*b,c*). Interestingly, after quantification at the same time point, whilst the CRX levels were similar (FIG. 5*d*), the organization between the retinal pigmentation and the retinal tissue was significantly improved in the retinal organoids coming from the microwell organoid array culture (FIG. 5*e*). Furthermore, the retinal tissue in the organoids matured together with the pigmented epithelium and the polarity of the retina epithelium coming from the microwells was often reversed compared to the conventional culture (FIG. 5*f,g*). It was shown that real time fluorescent reporters appearing on 3D cellular structures could be tracked in real-time within the organoid array. The array of organoids could be overlaid by a regular tessellation, such that the organoids are uniquely positioned within adjacent tiles of the tessellation (FIG. 5*h, i*)

The inventors show that the methods of the present invention can be used to produce arrays of retinal organoid arrays suitable for high-throughput analysis, such as quantification of CRX expression.

3.3. Materials and Methods 3.3.1. Cell Culture

OCT4::GFP Mouse Embryonic Stem Cells (mESCs) provided by Austin Smith (University of Cambridge) were routinely expanded without feeders in Dulbecco's Modified Eagle Medium (DMEM) supplemented with leukemia inhibitory factor (LIF), ESC screened fetal bovine serum (FBS, Gibco) (15%) medium, Non-essential amino acids (NEAA) sodium pyruvate (10 mM) and b-mercaptoethanol (0.1 mM), hereafter referred as ES cell medium (Smith).

CRX::GFP Mouse Embryonic Stem Cells (mESCs) derived by Decembrini and colleagues were routinely maintained as reported previously (Decembrini et al., 2014).

3.3.2. Preparation of Retinal Organoids Microwell Arrays:

CRX::GFP mESCs6 were washed with phosphate-buffered saline (1×PBS, Gibco) and detached with trypsin (Gibco, Cat. n° 25200-056). The cells were then resuspended in Optic Vesicle (OV) induction medium at a density of 525'000 cells/mL in order to seed 3000 cells per microwell. The cell suspension was then added on top of the arrays, in the inner ring, and the cells were left to sediment for 30 minutes at 37° C. and 5% CO2. Then, 660 μL of OV induction medium was added outside the microwell array without disturbing the sedimented cells. After an overnight incubation, the cells formed aggregates in each microwell and 140 μL of a diluted growth factor reduced Matrigel™ solution (12%, Corning) was added in each 24 wells, to reach a final Matrigel™ concentration of 2%. The aggregated cells were left in OV induction medium for 7 days. At day 7, the medium was changed to Optic Cup (OC) induction medium6 and left until day 12. At day 12, the medium was subsequently changed to Retina Maturation medium6 until day 30. In this case the medium was changed every other day. Additionally, the organoids were incubated at 40% oxygen from day 12 on, to promote the survival of newly born photoreceptors.

Example 4. Human Adult Colorectal Tumor Organoid Arrays 4.1. Introduction

Cancer in vitro models are expected to become potent models, if they are demonstrated to behave in vitro similarly to the native cancerogenic tissue in vivo. Tumors are a heterogeneous collection of cells, including cancer stem cells, which disrupts the native tissue. This Example demonstrates the production of microarrays from human colorectal tumor biopsies, a disease that stands as one of the most widely spread cancers, 4.2. Results and Discussion Primary human colorectal tumors biopsy samples can be cultured and grown for extended periods of time (FIG. 6*a*). To avoid losing the heterogeneity of each tumor aggregate, cells are dissociated to single cells and re-aggregated from multiple cells in microwells at every passage. The resulting spheroids retain viability (FIG. 6*b*) and double every 7 days, similarly to when they are cultured in Matrigel™ drop. Moreover, the different culture conditions modify the polarity of the tumoroids (FIG. 6*c*). These cancer organoids could be maintained and grown in a Matrigel™ free environment for more than 15 passages. Their growth was variable over extended periods, but, in average, the cell population doubled every 7 days (FIG. 6*d*).

The diameter of the microwell has an influence on the growth of the tumoroids. Indeed, for equal numbers of cells seeded per microwells, the bigger diameter allowed the spheroid to grow more extensively. This effect was conserved over two different cell densities per microwell (FIG. 6*e*).

The method of producing tumoroid arrays described herein enables modification and fine-tuning of the local microenvironment, thereby enabling control of tumoroid behavior in the tumoroid array. Cell survival in the microwell arrays could be tracked using live/dead fluorescence assays and the organization of the organoids analyzed using immunofluorescence.

4.3. Materials and Methods 4.3.1. Cell Culture

Human colorectal cancer organoids (a generous gift from Dr. Ordonez Moran Paloma, from Prof. Huelsken group, EPFL) were routinely passaged in Matrigel™ as previously reported (Jung et al., 2011).

4.3.2. Preparation of Colorectal Cancer Organoid Microwell Arrays

Human colorectal cancer organoids were released from Matrigel™ in cold basal medium (advanced DMEM/F-12 containing 1 mM HEPES, Glutamax™ and 1% P/S). The organoids were spun down at 800 rpm, for 4 minutes, at 4° C. and resuspended in 1 mL of cell dissociation solution (TrypLE, 2 mg/mL DNAse I, Gibco, 1 mM N-acetylcysteine and 10 μM Y27632). Cells were dissociated for 8 minutes at 37° C. and subsequently washed with basal medium containing 10% foetal bovine serum (FBS, heat inactivated, Gibco). After centrifugation at 1000 rpm, for 4 minutes, at 4° C., the cells were resuspended at a density of $2.24\times10^5$ cells/mL in colorectal cancer organoid medium supplemented with 2.5 μM Thiazovivin in order to deposit 100 cells per microwell. 50 μL of the cell suspension was added in each microwell. Cells settled down by gravitational sedimentation for 30 minutes at 37° C. and 5% $CO_2$ and 700 μL of colorectal cancer organoid medium were then added. The cells were kept for 7 days and the medium was changed every four days.

Example 5. Human Mammary Gland Organoid Arrays 5.1. Introduction

It was assessed whether human-derived cell lines could be grown in three dimensions on the microwell arrays, focusing on a human breast epithelial cell line (MCF10A), which, when cultured in Matrigel™ drops or sandwich assays, form acini, that can represent some features of the human breast mammary glands.

5.2. Results and Discussion

MCF10A cells grown in a Matrigel™ phase from single or a few cells can be used to form arrays (FIG. 7*a*). The resulting structures are polarized from the localization of cell nuclei at the outside of the colony, a focalization of the F-actin signal inside as well as the restricted laminin signal at the outer border of the colony. GM130, a Golgi protein, co-localizes with the edges of the nuclei (FIG. 7*b*). This phenotype indicates that the cellular structures are mimicking the organization of acini in vivo, and therefore provides an elegant model for breast cancer drug screening.

Breast cancer phenotypes can be modeled by introduction of mutations in these arrays and analyzed further after treatment with specific drugs. The microwell arrays allow for histological sectioning and guaranties that all the cell structures lie on one plane, which strongly simplifies the sectioning. It was shown that the clusters in the array are indeed on one plane such that it is very easy to perform high content imaging using this technique (FIG. 7*c*).

5.3. Material and Methods 5.3.1. Cell Culture

MCF10a breast epithelial cells were routinely passaged in standard monolayer cultures as previously reported (Debnath et al., 2003).

5.3.2. Preparation of MCF10a Acini Microwell Arrays

Cells were detached with trypsin (TrypLE, Life Technologies). Cell suspensions with specific densities were prepared (e.g. $1.12\times10^6$ cells/mL, $2.24\times10^5$ cells/mL, and 2240 cells/mL for achieving 500 cells/microwell, 100 cells/microwell and 1 cell/microwell, respectively) in the cell-type specific media. Subsequently, 50 μL of the prepared cell solution was added in the inner ring containing the microwell arrays. Cells settled down by gravitational sedimentation for 30 minutes at 37° C. and 5% $CO_2$ and 700 μL of Assay medium were then added. The cells were kept 14 days in Assay medium and the medium was changed every four days.

Example 6. Human Small Intestine and Colon Organoids Arrays 6.1. Introduction It was assessed whether human stem cells from the gastro-intestinal tract (i.e. small intestine and colon), reported by Hannan and colleagues (Hannan et al, 2013) and Sato and colleagues (Sato et al, 2009), could be grown and differentiated in three dimensions as organoids on the microwell arrays. iPS-derived progenitors are of major interest as they could avoid sampling biological material on patients and could serve with matched accuracy for drug discovery as well as patient diagnostics. On the other hand, extracted adult colon stem cells, grown as organoids, are of high interest to mimic closely organ-specific phenotype of patients of interest.

6.2. Results and Discussion

By seeding a single cell suspension (i.e. 100 cells per microwell) in stem cell expansion medium supplemented with 2% Matrigel, we could form iPS-derived intestinal stem cell colonies or colon stem cell colonies at the bottom of each microcavity (FIG. 8*a,d*). We could observe that the cells were able to sediment, aggregate efficiently and form colonies overnight. The stem cell colonies were then expanded for another two days to form luminal and cystic colonies that harbor a thin epithelium of stem cells (FIG. 8*b,e*). At day 3, the colonies reached a size, thus a number of cells that would support their differentiation (FIG. 8*b,e*). The medium was thus changed at day 3 to differentiation medium (see Material and Methods 6.3). After already two day of differentiation the stem cell colonies undergo a morphological change towards harboring a thicker epithelium, starting to collapse and forming bud-like structures (FIG. 8*c,f*).

6.3. Material and Methods 6.3.1. Cell Culture iPS-derived foregut organoids were derived as described previously (Hannan et al 2014). The organoids were maintained in matrigel drops and passaged every 7 days. The stem cell expansion medium was changed every other day. Adult colon organoids were extracted and maintained as described previously (Sato et al). The organoids were maintained in matrigel drops and passaged every 7-10 days. The stem cells expansion medium was changed every 2-3 days.

6.3.2. Preparation of iPS-Derived Intestinal Organoid Arrays iPS-derived foregut organoid arrays were prepared and seeded using the same procedure as the LGR5::GFP mouse intestinal organoids arrays (see example 2, sub-chapter 2.4.2). Here, after overnight aggregation, an extra 700 μL of stem cell expansion medium was added. At day 3 the medium was switched to differentiation medium, i.e. stem cell expansion medium without Wnt3A and Nicotinamide.

Example 7. Mouse Intestinal Organoids Cannot Form from Aggregated Single Cells onto Aggrewell™ Microwells 7.1. Introduction Microwells designed for the generation of EBs have been commercialized over the past decade. One of the most used technologies for this purpose is Aggrewell™, that consists of pyramidal microwells of either 400 μm or 800 μm. This technology has shown the capacity to generate EBs on a period of 24-48 hours, however, there are no reports showing the possibility to perform long-term stem cell culture and organoid culture using this technology. Here, we assessed whether a very well described organoid system, such as mouse intestinal organoids, could be grown on an Aggrewell™ platform.

7.2. Results and Discussion

After preparing the cells as described in the Material and Methods section (7.3), we seeded the appropriate cell suspension on the Aggrewell™ microwells following the manufacturer instructions. The manufacturer indicates that the microwells have to be coated before the addition of the cells using their dedicated product, the Aggrewell™ rinsing solution. Thus, we decided to coat half the plate and leave the other half of the plate uncoated as a control. Then, we seeded the cells and attempted to form mouse intestinal organoid arrays on Aggrewell™ microwells following our novel procedure (see example 2, subchapter 2.4.2).

After expanding the intestinal stem cells as colonies for two days in ENRCV, we could already see that in the uncoated condition, cells were attaching to the plastic surface and starting to make adherent colonies (see FIG. 9*a*, blue arrows; numbering the wells from top left to bottom right, wells 6 and 10) and then monolayers of differentiated cells (see FIG. 9*a*, red arrows; numbering the wells from top left to bottom right, wells 1 and 7). On the other hand, when the Aggrewell™ microwells were coated the cells were just growing in suspension above the microwell arrays in a very disorganized way and it was impossible to generate a stable and sound organoid array (see FIG. 9*b*, arrows). Here, we could demonstrate that hard substrates, such as plastics or polydimethylsiloxane (PDMS), are not sufficient for the generation of mouse intestinal organoid arrays.

7.3. Materials and Methods 7.3.1. Cell Culture

LGR5::GFP mouse Intestinal Stem Cells: Crypts were extracted from murine small intestine as reported previously (Sato, 2009). The isolated crypts were maintained and expanded in Matrigel™, in self-renewal medium, ENR-CV (Yin, 2014).

7.3.2. Preparation of Intestinal Organoid Arrays onto Aggrewell™ Microwells

LGR5::GFP intestinal stem cells were prepared as described in examples 2, subchapter 2.4.2. In order to deposit 100 cells per 800 μm pyramidal microwell, 2 mL of the appropriate cell suspension was added in each well as indicated by the manufacturer's product information sheet. The cells were aggregated overnight in medium containing a dilute non-gelling basal lamina component. The aggregated mISCs were expanded in self-renewal conditions for 2 days, and the organoids were differentiated for 4 days in differentiation medium (ENR). Growth factors were replenished every other day.

Example 8. Mouse Retinal Organoids Cannot Differentiate Efficiently from Aggregated Single Cells onto Aggrewell™ Microwells 8.1. Introduction Similarly to the example 7, microwells designed for the generation of EBs have been commercialized over the past decade. One of the most used technologies for this purpose is Aggrewell™, that consists of pyramidal microwells of either 400 μm or 800 μm. This technology has shown the capacity to generate EBs on a period of 24-48 hours, however, there are no reports showing the possibility to perform long-term stem cell culture and organoid culture using this technology. Here, we assessed whether a pluripotent stem cell-derived organoid system, such as mouse retinal organoids, could be grown on the Aggrewell™ platform.

8.2. Results and Discussion

Using the biggest available size of commercially available pyramidal microwells, i.e. 800 μm, we attempted to generate mESCs aggregates and further retinal organoids from the CRX::GFP mouse Embryonic Stem Cell line reported by Decembrini et al. After performing the seeding following the manufacturer's product information sheet, we let the cells aggregate overnight according to published protocols. After this first step, we could already observe that both the substrate and the unnatural shape were inhibiting the cells to form compacted and sound aggregates (see FIG. 10). This incapacity to reliably form aggregates impaired the continuation of the protocol and thus the differentiation of the cells into retinal organoids. Similarly to the example 7, we could observe that both the shape and the substrate are critical components for making sound arrays of mouse retinal organoids.

8.3. Material and Methods 8.3.1. Cell Culture

CRX::GFP Mouse Embryonic Stem Cells (mESCs) derived by Decembrini and colleagues were routinely maintained as reported previously (Decembrini, 2014).

8.3.2. Preparation of Retinal Organoid Arrays onto Aggrewell Microwells

CRX::GFP mESCs (Decembrini, 2014) were prepared as described in example 3. In order to deposit 3000 cells per 800 μm pyramidal microwell, 2 mL of the appropriate cell suspension was added in each well as indicated by the manufacturer's product information sheet and left overnight to sediment. The cells were further cultured as described in example 3.

REFERENCES

Abberton, K. M., Bortolotto, S. K., Woods, A. A., Findlay, M., Morrison, W. A., Thompson, E. W., and Messina, A. (2008). Myogel, a novel, basement membrane-rich, extracellular matrix derived from skeletal muscle, is highly adipogenic in vivo and in vitro. Cells Tissues Organs 188, 347-358.

Allbritton, N. L., Wang, Y., Gunasekara, D., Ahmad, A. A., Magness, S. T., and Sims, C. E. (2015). Colonic organoid array on a biomimetic, microengineered hydrogel scaffold. (Gyeongju, Korea), p.

Brandenberg, N., and Lutolf, M. P. (2016). In Situ Patterning of Microfluidic Networks in 3D Cell-Laden Hydrogels. Adv. Mater. 28, 7450-7456.

Debnath, J., Muthuswamy, S. K., and Brugge, J. S. (2003). Morphogenesis and oncogenesis of MCF-10A mammary epithelial acini grown in three-dimensional basement membrane cultures. Methods San Diego Calif. 30, 256-268.

Decembrini, S., Koch, U., Radtke, F., Moulin, A., and Arsenijevic, Y. (2014). Derivation of Traceable and Transplantable Photoreceptors from Mouse Embryonic Stem Cells. Stem Cell Rep. 2,853-865.

Decembrini, S., Brandenberg, N., Hoehnel, S., Arsenijevic, Y., and Lutolf, M. P. (2016). Micro-culture arrays to control the generation of retinal organoids. In ARVO 2016 Annual Meeting, p.

Dekkers, J. F., Wiegerinck, C. L., de Jonge, H. R., Bronsveld, I., Janssens, H. M., de Winter-de Groot, K. M., Brandsma, A. M., de Jong, N. W. M., Bijvelds, M. J. C., Scholte, B. J., et al. (2013). A functional CFTR assay using primary cystic fibrosis intestinal organoids. Nat. Med. 19, 939-945.

Ehrbar, M., Rizzi, S. C., Hlushchuk, R., Djonov, V., Zisch, A. H., Hubbell, J. A., Weber, F. E., and Lutolf, M. P. (2007a). Enzymatic formation of modular cell-instructive fibrin analogs for tissue engineering. Biomaterials 28, 3856-3866.

Ehrbar, M., Rizzi, S. C., Schoenmakers, R. G., San Miguel, B., Hubbell, J. A., Weber, F. E., and Lutolf, M. P. (2007b). Biomolecular Hydrogels Formed and Degraded via Site-Specific Enzymatic Reactions. Biomacromolecules 8, 3000-3007.

Ehrbar, M., Sala, A., Lienemann, P., Ranga, A., Mosiewicz, K., Bittermann, A., Rizzi, S. C., Weber, F. E., and Lutolf, M. P. (2011). Elucidating the Role of Matrix Stiffness in 3D Cell Migration and Remodeling. Biophys. J. 100, 284-293.

Fatehullah, A., Tan, S. H., and Barker, N. (2016). Organoids as an in vitro model of human development and disease. Nat. Cell Biol. 18, 246-254.

Gobaa, S., Hoehnel, S., Roccio, M., Negro, A., Kobel, S., and Lutolf, M. P. (2011). Artificial niche microarrays for probing single stem cell fate in high throughput. Nat. Methods 8, 949-955.

Gracz, A. D., Williamson, I. A., Roche, K. C., Johnston, M. J., Wang, F., Wang, Y., Attayek, P. J., Balowski, J., Liu, X. F., Laurenza, R. J., et al. (2015). A high-throughput platform for stem cell niche co-cultures and downstream gene expression analysis. Nat. Cell Biol. 17, 340-349.

Hannan, N. R. et al. Generation of multipotent foregut stem cells from human pluripotent stem cells. Stem cell reports 1, 293-306, doi:10.1016/j.stemcr.2013.09.003 (2013).

Hohnel, S., Brandenberg, N., and Lutolf, M. (2016). Devices for High-Throughput Aggregation and Manipulation of Mammalian Cells.

Jourdain, P., Becq, F., Lengacher, S., Boinot, C., Magistretti, P. J., and Marquet, P. (2014). The human CFTR protein expressed in CHO cells activates aquaporin-3 in a cAMP-dependent pathway: study by digital holographic microscopy. J Cell Sci 127, 546-556.

Jung, P., Sato, T., Merlos-Suarez, A., Barriga, F. M., Iglesias, M., Rossell, D., Auer, H., Gallardo, M., Blasco, M. A., Sancho, E., et al. (2011). Isolation and in vitro expansion of human colonic stem cells. Nat. Med. 17, 1225-1227.

Lo, Y.-H., Chiu, Y., and Cai, W. (2016). Position-Defined Cell Culture and Characterization Platform.

Rivron, N. C., Rouwkema, J., Truckenmuller, R., Le, G. S., Blitterswijk, C. A., Vrij, E. J., Rivron, N. C., Le, G. S., and Van, B. C. A. (2011). Self-Assembling Tissue Modules.

Sato, T., Vries, R. G., Snippert, H. J., van de Wetering, M., Barker, N., Stange, D. E., van Es, J. H., Abo, A., Kujala, P., Peters, P. J., et al. (2009). Single Lgr5 stem cells build crypt-villus structures in vitro without a mesenchymal niche. Nature 459, 262-265.

Shamir, E. R., and Ewald, A. J. (2014). Three-dimensional organotypic culture: experimental models of mammalian biology and disease. Nat. Rev. Mol. Cell Biol. 15, 647-664.

Smith, A. G. Culture and differentiation of embryonic stem cells. J. Tissue Cult. Methods 13, 89-94.

Todhunter, M. E., Jee, N. Y., Hughes, A. J., Coyle, M. C., Cerchiari, A., Farlow, J., Garbe, J. C., LaBarge, M. A., Desai, T. A., and Gartner, Z. J. (2015). Programmed synthesis of three-dimensional tissues. Nat. Methods 12, 975-981.

Vrij et al (2016) 3D high throughput screening and profiling of embryoid bodies in thermoformed microwell plates, LAB ON A CHIP: MINIATURISATION FOR CHEMISTRY, PHYSICS, BIOLOGY, MATERIALS SCIENCE AND BIOENGINEERING, vol. 16, no. 4, 1 Jan. 2016 (2016-01-01), pages 734-742

Yin, X., Farin, H. F., van Es, J. H., Clevers, H., Langer, R., and Karp, J. M. (2014). Niche-independent high-purity cultures of Lgr5+ intestinal stem cells and their progeny. Nat. Methods 11, 106-112.

The invention claimed is:

1. A method for making an array of organoids, comprising:

i. seeding stem cells on a surface;

ii. culturing the stem cells of step i. in situ to allow their aggregation into multicellular stem cell containing aggregates, iii. overlaying the multicellular aggregates of step ii. with an overlay comprising an overlay hydrogel; and iv. culturing the multicellular stem cell containing aggregates of step ii. in situ in conditions suitable for organoid development, wherein the array of organoids is within a single focal plane and the surface may be overlaid with a regular tessellation, such that the organoids are uniquely positioned within adjacent tiles of the tessellation; wherein the organoids are composed of organ specific cells that are self-organized wherein the surface is a biofunctional hydrogel imprinted with cavities or microwells of various sizes, shapes and depths;

wherein steps ii., iii., and iv. occur in situ such that the stem cells containing aggregates and the multicellular stem cell containing aggregates remain in the same position and/or culture environment from initiation to formation of the array of organoids; and wherein the biofunctional hydrogel of the surface has a stiffness between 150 Pa and 50 kPa and the hydrogel of the overlay is diluted such that it forms a viscous solution or semi-solid media.

2. The method of claim 1, wherein non-stem cells are seeded in combination with the stem cells seeded in step i.

3. The method of claim 2, wherein the surface hydrogel and/or overlay hydrogel comprises naturally derived biomaterials, wherein the naturally derived biomaterials are selected from the group comprising:

i. polysaccharides, gelatinous proteins, ECM components comprising: agarose; alginate; chitosan; dextran; gelatin; laminins; collagens; hyaluronan; fibrin, and mixtures thereof; or ii. a gel derived from natural ECM.

4. The method of claim 2, wherein the surface hydrogel and/or overlay hydrogel is a crosslinked macromolecule of hydrophilic polymers, wherein the polymers are linear or branched, and wherein the polymers are synthetic.

5. The method of claim 4, wherein the synthetic polymers are selected from the group comprising: poly(ethylene glycol), polyaliphatic polyurethanes, polyether polyurethanes, polyester polyurethanes, polyethylene copolymers, polyamides, polyvinyl alcohols, poly(ethylene oxide), polypropylene oxide, polyethylene glycol, polypropylene glycol, polytetramethylene oxide, polyvinyl pyrrolidone, polyacrylamide, poly(hydroxy ethyl acrylate), poly(hydroxyethyl methacrylate) and mixtures thereof.

6. The method of claim 2, the polymer is a branched poly(ethylene glycol)-based macromolecule.

7. The method of claim 1, wherein the surface comprises an array of microwells, wherein each microwell in the array is capable of supporting:

i. aggregation of defined numbers of stem cells into a multicellular aggregate of pre-defined size and shape, ii. spatially confined cell expansion, and/or iii. self-organization of stem cells and organoid development, wherein the microwell restricts movement of a developing organoid such that the centre of mass of the organoid is less than 100 μm from the center of the bottom of the microwell; and wherein each microwell is round-bottomed.

8. The method of claim 7, wherein each microwell has a diameter of about 10 μm to about 5 mm, wherein each microwell has a curvature radius of about 5 μm to about 2.5 mm, wherein each microwell has a depth of about 10 μm to about 6 mm, wherein the depth of the microwell is 1.2 times the diameter of the microwell.

9. The method of claim 7, wherein the surface comprises one or more bioactive factors that promote stem cell expansion, differentiation, self-organization and/or organoid development, wherein the one or more bioactive factors are extracellular matrix factors and/or proteins of major signalling pathways, wherein the bioactive factors are proteoglycans, non-proteoglycan polysaccharides or fibrous proteins, wherein the one or more bioactive factors are provided on the surface of each microwell, wherein the one or more bioactive factors are delivered to the surface of each microwells by diffusion from one or more microchannels in the surface, and wherein the one or more microchannels are positioned within the surface on either or on both sides of each microwell.

* * * * *